United States Patent [19]

Heeres et al.

[11] Patent Number: 4,619,931

[45] Date of Patent: Oct. 28, 1986

[54] [[4-[4-(4-PHENYL-1-PIPERAZINYL)-PHENOXYMETHYL]-1,3-DIOXOLAN-2-YL]METHYL]-1H-IMIDAZOLES AND 1H-1,2,4-TRIAZOLES

[75] Inventors: Jan Heeres, Vosselaar; Raymond A. Stokbroekx, Beerse; Leo J. J. Backx, Arendonk, all of Belgium

[73] Assignee: Janssen Pharmaceutica, N.V., Beerse, Belgium

[21] Appl. No.: 569,122

[22] Filed: Jan. 9, 1984

Related U.S. Application Data

[63] Continuation-in-part of Ser. No. 470,405, Feb. 28, 1983, abandoned.

[51] Int. Cl.$^4$ .................. C07D 403/14; A61K 31/495
[52] U.S. Cl. ..................................... 514/252; 544/366; 544/360

[58] Field of Search ................. 544/366, 370; 424/250

[56] References Cited

U.S. PATENT DOCUMENTS

| 4,144,346 | 3/1979 | Heeres et al. | 544/370 |
| 4,267,179 | 5/1981 | Heeres et al. | 544/366 |
| 4,335,125 | 6/1982 | Heeres et al. | 544/370 |
| 4,368,200 | 1/1983 | Heeres et al. | 544/366 |
| 4,503,055 | 3/1985 | Heeres et al. | 544/370 |

Primary Examiner—George F. Lesmes
Assistant Examiner—S. A. Gibson
Attorney, Agent, or Firm—Geoffrey G. Dellenbaugh

[57] ABSTRACT

Substituted [[4-[4-(4-phenyl-1-piperazinyl)phenoxymethyl]-1,3-dioxolan-2-yl]methyl]-1H-imidazoles and 1H-1,2,4-triazoles having antimicrobial properties and being particularly useful in the treatment of vaginal candidosis.

3 Claims, No Drawings

[[4-[4-(4-PHENYL-1-PIPERAZINYL)PHENOXYMETHYL]-1,3-DIOXOLAN-2-YL]METHYL]-1H-IMIDAZOLES AND 1H-1,2,4-TRIAZOLES

CROSS-REFERENCE TO RELATED APPLICATIONS

This is a continuation-in-part of our co-pending application Ser. No. 470,405 filed Feb. 28, 1983 now abandoned.

BACKGROUND OF THE INVENTION

In U.S. Pat. No. 4,144,346 there are described a number of 1-(1,3-dioxolan-2-ylmethyl)-1H-imidazoles and 1H-1,2,4-triazoles and in U.S. Pat. No. 4,267,179 there are described a number of heterocyclic derivatives of (4-phenyl-1-piperazinyl-aryloxymethyl-1,3-dioxolan-2-yl)methyl-1H-imidazoles and 1H-1,2,4-triazoles, which are taught to have antifungal and antibacterial properties.

In comparison with the prior art compounds, the subject compounds of the present invention differ therefrom not only by their chemical structure but also by their increased effectiveness in the inhibition of the growth of *Candida albicans* after systemic and/or topical administration, which effectiveness make them especially useful in the treatment of vaginal candidosis by topical and/or systemic administration.

DESCRIPTION OF THE PREFERRED EMBODIMENTS

This invention is concerned with 1H-imidazoles and 1H-1,2,4-triazoles having the formula

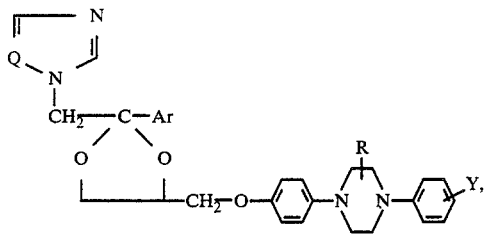

the pharmaceutically acceptable acid-addition salts and the stereochemically isomeric forms thereof, wherein Q is —N= or —CH=;

Ar is phenyl or substituted phenyl, said substituted phenyl having from 1 to 3 substituents each independently selected from the group consisting of halo, lower alkyl, lower alkyloxy, nitro, amino and trifluoromethyl;

R is hydrogen or lower alkyl; and

Y is a radical having the formula

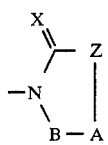

or a radical having the formula

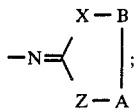

wherein

Z is O or $NR^1$;

said $R^1$ being hydrogen; lower alkenyl; lower alkynyl; Ar; cycloalkyl; lower alkyl optionally substituted with a member selected from the group consisting of Ar, lower alkyloxy and cycloalkyl; pyrimidine, optionally substituted with up to two substituents selected from the group consisting of lower alkyl, amino, nitro, hydroxy, lower alkyloxy, lower alkylthio, halo, phenyl, carboxyl and lower alkyloxycarbonyl;

X is O, S or $NR^2$;

said $R^2$ being hydrogen or lower alkyl;

A is >C=O, $NR^3$ or methylene, optionally substituted with up to two radicals selected from the group consisting of lower alkyl and Ar;

said $R^3$ being hydrogen or lower alkyl, or $R^1$ and $R^3$, taken together, form a lower alkanediyl radical;

provided that, when A is $NR^3$, Z is other than oxygen; and

B is >C=O or methylene optionally substituted with up to two radicals selected from the group consisting of lower alkyl and lower alkyloxy;

or A and B, taken together, form a bivalent radical of formula:

 (c),

 (d)

or

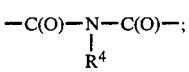 (e)

wherein $R^4$ is hydrogen or lower alkyl; or where Y is a radical of formula (b), A and B, when taken together, can also form a bivalent radical of formula

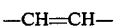 (f)

or

 (g);

wherein one hydrogen in the said radical (g) and up to two hydrogens in the said radicals (c), (d) or (f) may be replaced by a lower alkyl radical;

provided than when —A—B— is a radical of formula (g), said radical is connected to Z by its nitrogen atom and Z is other than 0.

In the foregoing definitions the term "halo" is generic to fluoro, chloro, bromo and iodo; the term "lower alkyl" is meant to include straight and branched hydrocarbon radicals having from 1 to 6 carbon atoms such as, for example, methyl, ethyl, 1-methylethyl, 1,1-dimethylethyl, propyl, 1-methylpropyl, 2-methylpropyl, butyl, pentyl, hexyl and the like; "lower alkenyl" refers to alkenyl radicals having from 2 to about 6 carbon atoms, such as, for example, 2-propenyl, 2-butenyl, 3-butenyl, 2-pentenyl and the like; "lower alkynyl" refers to alkynyl radicals having from 2 to about 6 carbon atoms, such as, for example, 2-propynyl, 2-butynyl, 3-butynyl, 2-pentynyl and the like; "cycloalkyl" embraces cyclopropyl, cyclobutyl, cyclopentyl and cyclohexyl; and "lower alkanediyl" stands for bivalent straight or branch chained alkanediyl radicals having from 3 to 6 carbon atoms.

The compounds of formula (I) may contain in their structure a tautomeric system and consequently these compounds may be present in each of their tautomeric forms.

Preferred compounds within the invention are those wherein Y is a radical of formula (a) or (b), wherein X, Z, A and B are as described hereinabove, provided that A and B, taken together, do not form a radical of formula (f) or (g) when Y is a radical of formula (b).

The most preferred compounds within the invention are:

cis-1-butyl-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-imidazolidinedione;

cis-1-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-3-propyl-2-imidazolidinone; the pharmaceutically acceptable acid addition salts and the stereochemically isomeric forms thereof.

In order to simplify the structural representations of the compounds (I) and of certain starting materials and intermediates used in the preparation thereof, the 2-Ar-2-(1H-imidazol-1-ylmethyl or 1H-1,2,4-triazol-1-ylmethyl)-1,3-dioxolan-4-yl group, wherein Ar is as previously defined, will hereafter be represented by the symbol D:

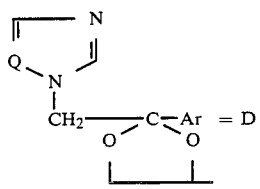

The compounds of formula (I) can generally be prepared by O-alkylating an appropriately substituted phenol of formula (III) with a reactive ester of formula (II).

D-CH₂—W +

(II)

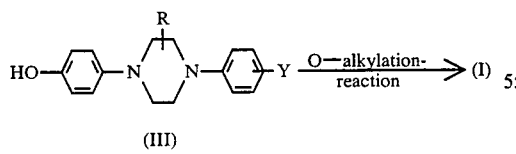

(III)

In formula (II), W has the meaning of a reactive ester residue such as, for example, halo, preferably chloro, bromo or iodo, or a sulfonyloxy group such as, for example, methylsulfonyloxy or 4-methylphenylsulfonyloxy and the like.

The said O-alkylation reaction is conveniently conducted in a suitable reaction-inert solvent or a mixture of such solvents. Suitable reacion-inert solvents are an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); hexamethylphosphoric triamide (HMPT); dimethyl sulfoxide (DMSO); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. It may be advantageous previously to convert the substituted phenol (III) into a metal salt thereof, preferably the sodium salt, in the usual manner, e.g., by the reaction of (III) with metal bases such as sodium hydride, sodium hydroxide and the like, and to use thereafter said metal salt in the reaction with (II). Somewhat elevated temperatures are appropriate to enhance the reaction rate and most preferably the reaction is carried out at from about 80° C. to about 130° C.

Additionally, the compounds of formula (I) may also generally be prepared by cyclizing an intermediate of formula (IV) with an amine of formula (V) or by cyclizing an amine of formula (VI) with an intermediate of formula (VII).

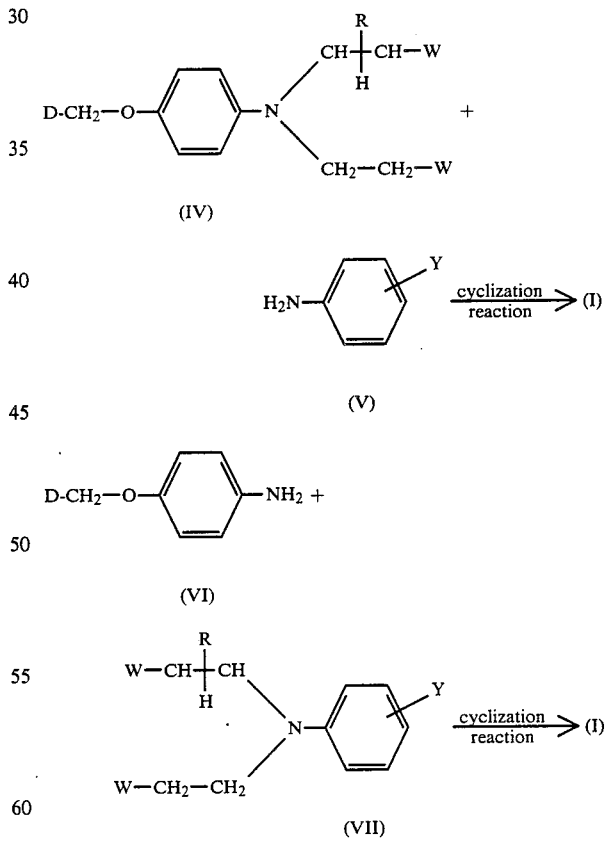

The reaction is carried out by stirring the reactants together in the presence of an appropriate polar solvent, e.g., water, in admixture with an appropriate water-miscible organic solvent such as, for example, 2-propanol, 2-propanone and the like, preferably at an elevated temperature, in order to enhance the rate of the reaction, and, most preferably, in the presence of an appropriate alkali- or earth alkali metal iodide such as, for example, potassium iodide.

The compounds of formula (I) can also be prepared by N-alkylating a piperazine of formula (VIII) with an appropriately substituted benzene of formula (IX) or by N-alkylating a piperazine of formula (XI) with a benzene of formula (X).

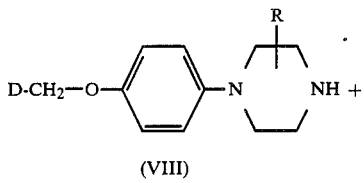

(VIII)

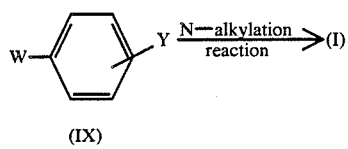

(IX)

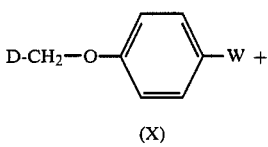

(X)

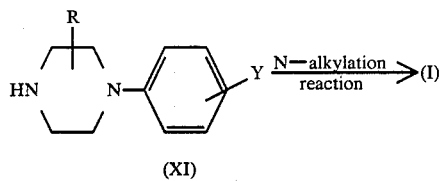

(XI)

Said N-alkylation reaction may be carried out in the usual manner, e.g., by stirring the reactants together, preferably at somewhat elevated temperatures in an appropriate organic solvent such as, for example, dimethylsulfoxide, N,N-dimethylformamide and the like, in the presence of an appropriate base such as, for example, an alkali metal hydride or carbonate.

The compounds of formula (I) may also be derived from a compound of formula

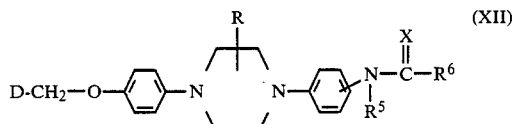

(XII)

wherein $R^5$ is hydrogen and $R^6$ is an appropriate leaving group or $R^5$ and $R^6$, when taken together, represent a direct bond, by cyclizing a said compound of formula (XII) with a derivative of formula

H-Z-A-B-L            (XIII), wherein L is an appropriate leaving group.

The said cyclization-reaction can generally be conducted in a suitable reaction-inert solvent such as, for example, an alcohol, e.g., butanol and the like, an ether, e.g., tetrahydrofuran, 1,4-dioxane and the like. Although the cyclization reaction may be conducted at room temperature, somewhat elevated temperatures are appropriate to enhance the rate of the reaction. Preferably the reaction is conducted at the reflux temperature of the reaction mixture. Suitable catalysts, e.g., N,N-dimethyl-4-pyridinamine, may also enhance the rate of the reaction.

In some cases it may be advantageous to conduct the hereinabove-described cyclization reaction with a derivative of formula

H-Z-A-B-L'           (XIV), wherein L' is a precursor of a leaving group, e.g. an alcohol function, to isolate the thus formed intermediate of formula

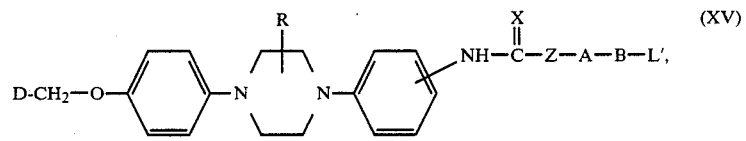

(XV)

to convert the L'-group into a suitable leaving group L, e.g. by converting an alcohol into a chloride function, and, finally, to cyclize the thus obtained intermediate of formula

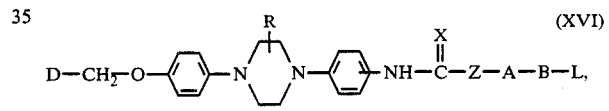

(XVI)

The compounds of formula (I) wherein Y is a radical of formula (a) wherein Z is $NR^1$, said compounds being represented by the formula (I-a), can also be prepared by cyclizing an intermediate of formula (XVII) with an appropriate reagent of formula (XVIII).

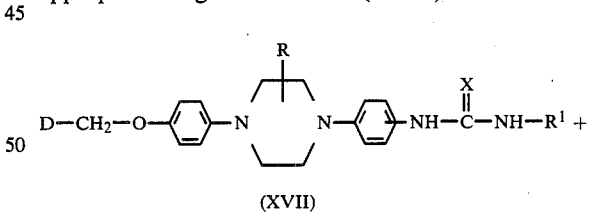

(XVII)

W—A—B—W           (XVIII)

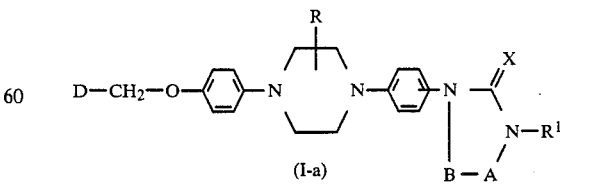

(I-a)

The said cyclization reaction is generally conducted following the same procedures as previously described herein for the preparation of (I) starting from (XII) and (XIII).

The compounds of formula (I), wherein Y is a radical of formula (b) wherein X is NR² and Z is NR¹, said compounds being represented by the formula (I-b) may be prepared by a cyclodesulfurization reaction of an intermediate of formula (XIX).

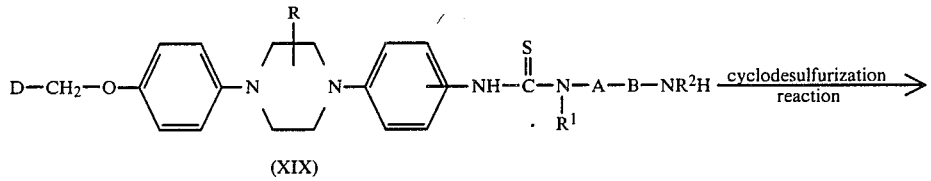

(XIX)

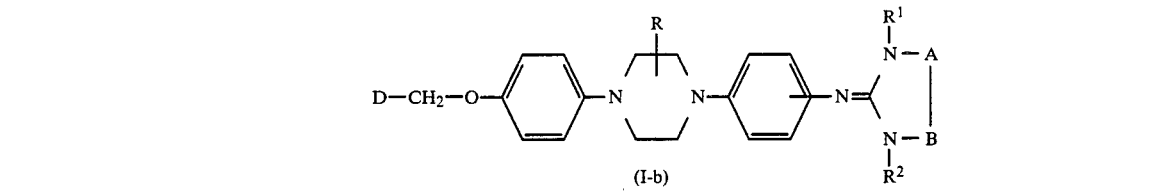

(I-b)

Said cyclodesulfurization reaction may be carried out by the reaction of (XIX) with an appropriate alkyl halide, preferably iodomethane in an appropriate reaction-inert organic solvent, e.g., a lower alkanol such as methanol, ethanol, 2-propanol and the like. Otherwise, the cyclodesulfurization reaction may be carried out by the reaction of (XIX) with an appropriate metal oxide or salt in an appropriate solvent according to art-known procedures. For example, the compounds of formula (I) can easily be prepared by the reaction of (XIX) with an appropriate Hg(II) or Pb(II) oxide or salt, such as, for example HgO, HgCl₂, Hg(OAc)₂, PbO or Pb(OAc)₂. In certain instances it may be appropriate to supplement the reaction mixture with a small amount of sulfur. Even so methanediimines, especially N,N'-methanetetraylbis[cyclohexanamine] may be used as cyclodesulfurizing agents.

The compounds of formula (I) wherein Y is a radical of formula (b), wherein -AB- is a bivalent radical of formula (g), said compounds being represented by the formula (I-c), can be prepared by reacting an intermediate of formula (XX) in an acidic aqueous solution, e.g. an aqueous hydrochloric, hydrobromic, sulfuric and the like acidic solution with a carbonyl-generating agent, e.g., formic acid and the like.

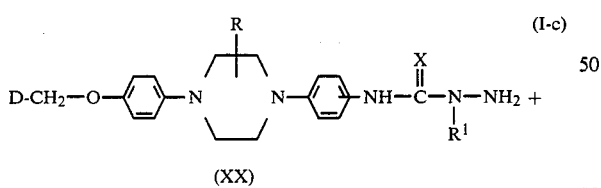

(XX)

carbonyl-generating agent ⟶

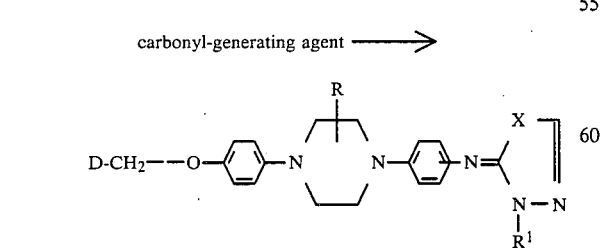

The compounds of formula (I) wherein Z is NH, said compounds being represented by the formulae (I-d-1) respectively (I-d-2) can be converted into a compound of formula (I) wherein R¹ is other than hydrogen, said R¹ being represented by the formula R¹⁻ᵃ and said compounds by the formulae (I-e-1) respectively (I-e-2) by reacting the former with a reagent of formula (XXI), wherein W represents a reactive leaving group, following art-known N-alkylation reactions.

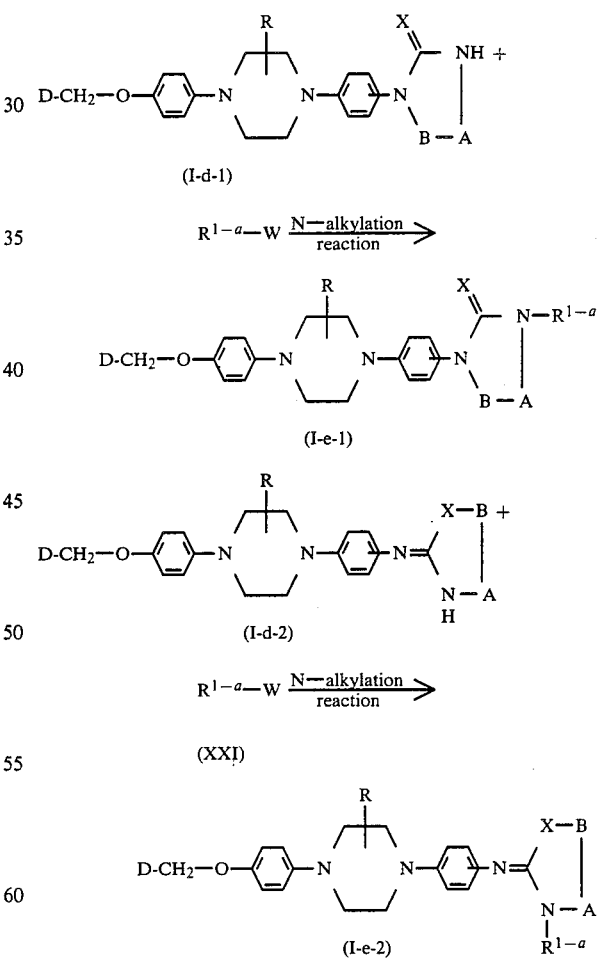

Said N-alkylation reaction may be carried out in the usual manner, e.g., by stirring the reactants together, preferably at somewhat elevated temperatures in an appropriate organic solvent such as, for example, dimethyl sulfoxide, N,N-dimethylformamide and the like, in the presence of an appropriate base such as, for example, an alkali metal hydride or carbonate.

The 1H-imidazole- and 1H-1,2,4-triazole-derivatives of formula (I), obtained in base form in the foregoing preparations, may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The salts are in turn converted to the corresponding free bases in the usual manner, e.g., by reaction with alkali such as sodium or potassium hydroxide.

From formula (I) it is evident that the compounds of this invention have at least two asymmetric carbon atoms in their structures, namely those located in the 2- and 4-position of the dioxolane nucleus, and consequently they can exist under different stereochemically isomeric forms. The stereochemically isomeric forms of (I) and the pharmaceutically acceptable acid addition salts thereof are intended to be embraced within the scope of this invention.

The diastereomeric racemates of (I), denoted as cis and trans forms respectively, according to the rules described in J. Org. Chem. 35 (9), 2849-2867 (1970), may be obtained separately by conventional methods. Appropriate methods which may advantageously be employed therefore include, for example, selective crystallization and chromatography separation, e.g., column-chromatography.

Since the stereochemical configuration is already fixed in a number of intermediate compounds, e.g., in intermediates of the formulas (II), (IV), (VI), (VIII), (X), (XII), (XV), (XVI), (XVII), (XIX) and (XX), it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereabove for the separation of cis and trans forms of the compounds (I).

It is evident that the cis and trans diastereomeric racemates may be further resolved into their optical isomers, cis(+), cis(−), trans (+) and trans(−) by the application of methodologies known to those skilled in the art.

A number of the intermediates and starting materials used in the foregoing preparations are known compounds, others may be prepared according to art-known methodologies of preparing similar compounds and some of them are novel and consequently their preparation will be described hereafter.

The intermediates of formula (III) can generally be derived from an intermediate of formula (XXII), wherein P is an appropriate protective group, following art-known procedures.

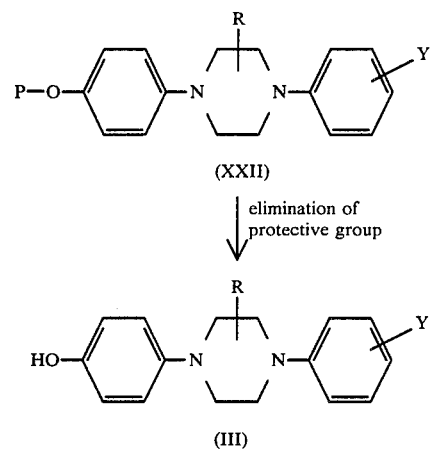

The procedures for eliminating the protective group P depend upon the nature of P. For example, where P is a methyl group the reaction can be conducted in an acidic hydrolyzing medium, containing a strong non-oxidizing mineral acid, e.g., hydrobromic acid in glacial acetic acid.

The intermediates of formula (XXII) can be obtained by cyclizing an intermediate of formula (XXIII) with an amine of formula (XX) following the same procedure as described for the preparation of (I) starting from (IV) and (V).

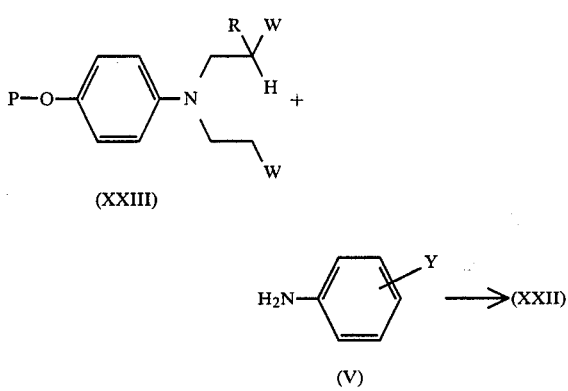

The starting materials of formula (V), wherein Y is a radical of formula (a) or (b) wherein Z is NR$^1$, said Y being represented by Y' and said (V) by (V-a), may be prepared by cyclizing a reagent of formula (XXIV) with a reagent of formula (XXV) following the cyclization reaction which is previously described herein for the preparation of the compounds of formula (I) starting from (XII) and (XIII).

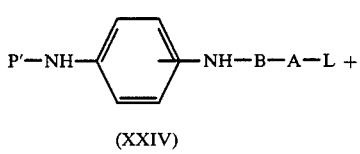

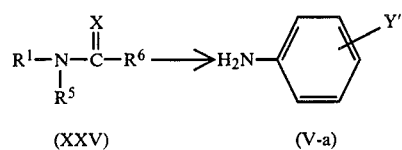

(XXV)  (V-a)

In (XXIV) P' represents hydrogen or an appropriate protective group, in which case the said protective group should be eliminated after the cyclization reaction.

The starting materials of formula (V) may also be derived from the corresponding nitro-derivatives following art-known nitro-to-amine reducing procedures.

The intermediate of formula (XXII) may also be derived from an intermediate of formula

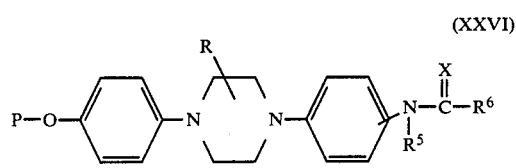

(XXVI)

by reacting the latter with a reagent of formula (XIII) following the previously described cyclization procedures for the preparation of compounds of formula (I) starting from (XII) and (XIII).

The intermediates of formula (XII) may be derived from an amine of formula (XXVII) by reacting the latter with a reagent of formula (XXVIII) or carbon disulfide thus yielding an intermediate of formula (XII-a), respectively an intermediate of formula (XII-b).

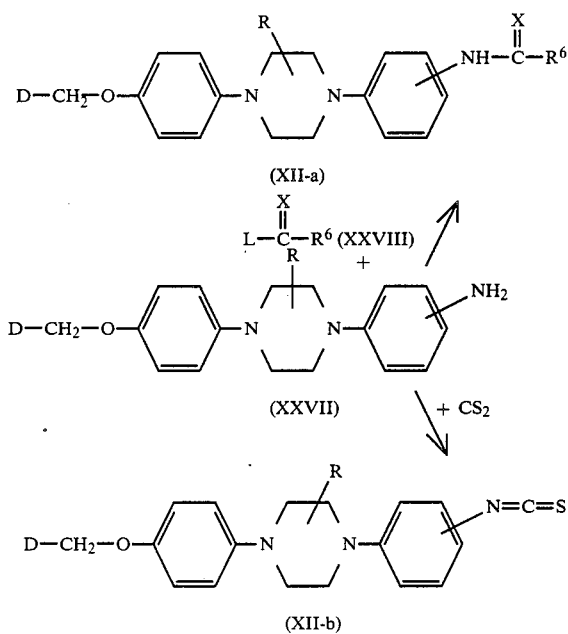

The intermediates of formula (XVII), (XIX) and (XX) can conveniently be prepared by reacting an intermediate of formula (XII) with an appropriate amine derivative.

The intermediates of formula (XII-a), wherein $R^6$ is a radical of formula $Z^1$-$R^7$, said intermediates being represented by the formula

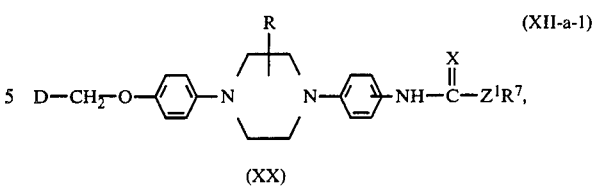

(XX)

wherein $Z^1$ is O or $NR^8$, said $R^8$ being hydrogen, Ar or lower alkyl optionally substituted by Ar, and $R^7$ is hydrogen, Ar, amino or lower alkyl optionally substituted by a member selected from the group consisting of hydroxy, Ar-amino, lower alkylamino or carboxy or substituted with up to two lower alkyloxy radicals, provided that:

$Z^1$ is other than O where $R^7$ is hydrogen; and where $R^7$ is amino, $Z^1$ is other than NH or O;

said intermediates, the pharmaceutically acceptable acid addition salts and the stereochemically isomeric forms thereof display strong antimicrobial properties themselves and both as useful intermediates herein and as antimicrobial substances they constitute an additional feature of this invention.

It is evident from the structure of the intermediates of formula (XII-a-1) that the stereochemical isomery as described hereinabove for the compounds of formula (I) applies also for the said intermediates and acid addition salts thereof.

The compounds of formula (I), the intermediates of formula (XII-a-1), the pharmaceutically acceptable acid addition salts and stereochemically isomeric forms thereof are useful agents in combatting fungi and bacteria. For example, said compounds are found to be highly active against a wide variety of fungi such as, for example, *Microsporum canis, Ctenomyces mentagrophytes, Trichophyton rubrum, Phialophora verrucosa, Cryptococcus neoformans, Candida tropicalis, Candida albicans, Mucor species, Aspergillus fumigatus, Sporotricum schenckii* and *Saprolegnia species,* and against bacteria such as, for example, *Erysipelotrix insidiosa,* Staphylococci such as *Staphylococcus hemolyticus* and Streptococci such as *Streptococcus pyogenes.* In view of their potent, local as well as systemic, antimicrobial activity the compounds of this invention constitute useful tools for the destruction or prevention of the growth of fungi and bacteria and more particularly they can effectively be used in the treatment of subjects suffering from such microorganisms.

The strong antimicrobial activity of the compounds (I) and the intermediates (XII-a-1) is clearly evidenced by the data obtained in the following experiments, which data are only given to illustrate the useful antimicrobial properties of all the compounds (I) and the intermediates (XII-a-1) and not to limit the invention either with respect to the scope of susceptible microorganisms nor with respect to the scope of formula (I) or (XII-a-1).

Experiment A: Oral treatment of vaginal candidosis in rats

Female Wistar rats of ±100 g body weight were used. They were ovariectomized and hysterectomized and after three weeks of recovery, 100 ug of oestradiol undecylate in sesame oil was given subcutaneously once a week for 3 consecutive weeks. The thus induced pseudo-oestrus was controlled by microscopic examination of vaginal smears. Food and water were left available ad libitum. The rats were infected intravaginally with $8.10^5$ cells of *Candida albicans*, grown on Sabouraud broth for 48 hours at 37° C. and diluted with saline. The date of infection varies from day +25 to day +32 after surgical intervention, depending on the appearance of signs of induced pseudo-oestrus.

The drugs under investigation were administered orally once a day for three days starting from the third day after infection. For each experiment there were placebo treated controls. The results were assessed by taking vaginal smears with sterile swabs on several days after the infection. The swabs were put into Sabouraud broth in petri-dishes and incubated for 48 hours at 37° C. If no growth of *Candida albicans* occurs, i.e., when the animals were negative at the end of the experiment, this was due to drug administration because it never happens in placebo-treated controls.

The first column in the Tables I, II and III give the lowest oral dose in mg/kg of the drug under investigation which is found active at the 14th day after infection.

Experiment B: Topical treatment of vaginal candidosis in rats

Female Wistar rats of ±100 g body weight were used. They were ovariectomized and hysterectomized and after three weeks of recovery, 100 ug of oestradiol undecylate in sesame oil was given subcutaneously once a week for 3 consecutive weeks. The thus induced pseudo-oestrus was controlled by microscopic examination of vaginal smears. Food and water were left available ad libitum. The rats were infected intravaginally with $8.10^5$ cells of *Candida albicans*, grown on Sabouraud broth for 48 hours at 37° C. and diluted with saline. The date of infection varies from day +25 to day +32 after surgical intervention, depending on the appearance of signs of inducing pseudo-oestrus.

The drugs under investigation were administered topically twice a day for three consecutive days starting from the third day after infection. For each experiment there were placebo treated controls. The results were assessed by taking vaginal smears with sterile swabs on several days after the infection. The swabs were put into Sabouraud broth in petri-dishes and incubated for 48 hours at 37° C. If no growth of *Candida albicans* occurs, i.e., when the animals were negative at the end of the experiment, this was due to drug administration because it never happens in placebo-treated controls.

The second column in the Tables I, II and III give the lowest concentration of the drug under investigation which is found active at the 7th day after the last topical administration of the drug.

Experiment C: Oral treatment of Microsporum canis infections in guinea pigs

Adult Albino guinea pigs were prepared by clipping their backs and infected on the scarified skin by scratching five 3 cm long transverse cuts with *Microsporum canis* (strain RV 14314). The animals were housed individually in wire mesh cages and food and water were available ad libitum. The drugs under investigation were administered orally once a day for 14 consecutive days starting 24 hours before infection. For each experiment there were placebo treated controls.

The animals were evaluated 21 days after infection by microscopic examination of the skin and by cultures on Sabouraud agar comprising a suitable bacterial antibiotic and a suitable agent to eliminate contaminating fungi.

The third column in Tables I, II and III give the lowest oral dose in mg/kg of the drug under investigation at which no lesions were observed and at which there was no culture growth.

Experiment D: Topical treatment of Microsporum canis infections in guinea pigs

Adult Albino guinea pigs were prepared by clipping their backs and infected on the scarified skin by scratching five 3 cm long transverse cuts with *Microsporum canis* (strain RV 14314). The animals were housed individually in wire mesh cages and food and water were available ad libitum. The drugs under investigation were administered topically once a day for 14 consecutive days starting the third day after infection. For each experiment there were placebo treated controls.

The animals were evaluated 21 days after infection by microscopic examination of the skin and by cultures on Sabouraud agar comprising a suitable bacterial antibiotic and a suitable agent to eliminate contaminating fungi.

The fourth column in Tables I, II and III gives the lowest concentration of the drug under investigation at which no lesions were observed and at which there was no culture growth.

The compounds listed in Tables I, II and III are intended to illustrate and not to limit the scope of the present invention.

TABLE I

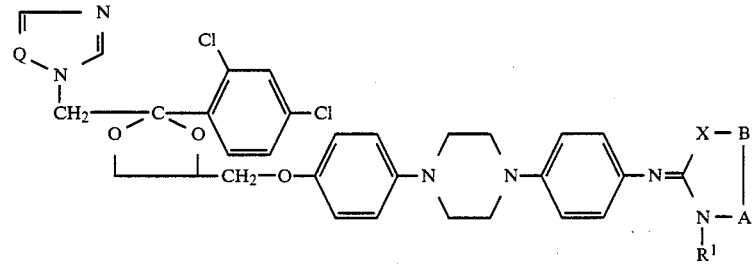

| Comp. No. | Q | X | B | A | R¹ | Vaginal candidosis in rats Lowest oral dose in mg/kg | Vaginal candidosis in rats Lowest topical concentration (%) | Microsporum canis infection Lowest oral dose in mg/kg | Microsporum canis infection Lowest topical concentration (%) |
|---|---|---|---|---|---|---|---|---|---|
| 142 | CH | O | CH₂ | CH₂ | C₂H₅ | 1.25 | 0.1 | <2.5 | 0.3 |
| 143 | N | O | CH₂ | CH₂ | CH₃ | 2.5 | 0.1 | 5 | 0.25 |

TABLE I-continued

| Comp. No. | Q | X | B | A | R¹ | Vaginal candidosis in rats Lowest oral dose in mg/kg | Vaginal candidosis in rats Lowest topical concentration (%) | *Microsporum canis* infection Lowest oral dose in mg/kg | *Microsporum canis* infection Lowest topical concentration (%) |
|---|---|---|---|---|---|---|---|---|---|
| 144 | N | O | CH₂ | CH₂ | C₂H₅ | 1.0 | 0.063 | 1.5 | ≧0.5 |
| 145 | N | O | CH₂ | CH₂ | n.C₃H₇ | — | 0.031 | 1.0 | 0.25 |
| 146 | N | O | CH₂ | CH₂ | n.C₄H₉ | 2.0 | 0.031 | 1.5 | 0.25 |
| 147 | N | O | CH₂ | CH₂ | i.C₃H₇ | — | 0.125 | 1.5 | 0.25 |
| 148 | N | O | CH₂ | CH₂ | C₂H₅(CH₃)CH | 1.25 | 0.031 | 0.5 | 0.25 |
| 141 | N | O | CH₂ | CH₂ | (C₂H₅)₂CH | 2.5 | 0.05 | 2.5 | 0.125 |
| 150 | N | O | CH₂ | CH₂ | C₂H₅(CH₃)CHCH₂ | 2.5 | 0.03 | 0.63 | 0.125 |
| 151 | N | O | CH₂ | CH₂ | i.C₄H₉ | 2.5 | 0.05 | 10 | 0.25 |
| 152 | N | O | CH₂ | CH₂ | n.C₃H₇(CH₃)CH | 1.25 | 0.031 | 2.5 | 0.125 |
| 119 | CH | S | CH₂ | CH₂ | C₂H₅ | — | 0.125 | 1.25 | 0.25 |
| 120 | CH | S | CH₂ | CH₂ | i.C₃H₇ | 1.25 | 0.125 | 1.25 | 0.25 |
| 153 | CH | O | CH₂ | CH₂ | C₂H₅(CH₃)CH | 1.25 | 0.03 | 2.5 | 0.5 |
| 157 | CH | S | CH₂ | CH₂ | i.C₄H₉ | — | 0.5 | 5 | <0.5 |
| 155 | CH | S | CH₂ | CH₂ | C₂H₅(CH₃)CH | — | <0.5 | 5 | 0.063 |
| 121 | N | S | CH₂ | CH₂ | C₂H₅ | 2.5 | 0.05 | 10 | 0.1 |
| 122 | N | S | CH₂ | CH₂ | C₂H₅(CH₃)CH | 2.5 | 0.05 | 1.25 | 0.1 |
| 123 | CH | S | CH₂ | CH₂ | i.C₅H₁₁ | — | — | 5 | — |
| 124 | CH | S | CH₂ | CH₂ | n.C₄H₉ | 2.5 | 0.125 | 1.25 | 0.5 |
| 125 | N | S | CH₂ | CH₂ | n.C₃H₇ | — | 0.125 | 1.25 | 0.25 |
| 126 | N | S | CH₂ | CH₂ | i.C₃H₇ | — | 0.5 | 1.25 | 0.1 |
| 127 | CH | S | CH₂ | CH₂ | CH₃ | 2.5 | 0.25 | 5 | <0.5 |
| 128 | N | S | CH₂ | CH₂ | i.C₄H₉ | — | 0.125 | <2.5 | 0.5 |
| 129 | CH | S | CH₂ | CH₂ | n.C₃H₇ | — | 0.125 | 5 | 0.25 |
| 130 | N | S | CH₂ | CH₂ | n.C₅H₁₁ | — | 0.25 | <2.5 | 0.25 |
| 118 | N | S | CH₂ | CH₂ | CH₃ | 2.5 | <0.125 | <2.5 | <0.5 |
| 131 | CH | S | CH₂ | CH₂ | n.C₅H₁₁ | 10 | 0.5 | 5 | 0.5 |
| 132 | CH | S | CH₂ | CH₂ | (C₂H₅)₂CH | 10 | 0.5 | 10 | <0.5 |
| 133 | CH | S | CH₂ | CH₂ | C₂H₅(CH₃)CHCH₂ | — | — | <10 | — |
| 53 | N | S | CH | CH | N—C₂H₅ | — | — | 10 | 0.5 |
| 54 | CH | S | CH | CH | N—C₂H₅ | — | — | 10 | 0.125 |
| 168 | CH | S | CHOCH₃ | CH₂ | N—CH₃ | — | 0.5 | 2.5 | 0.125 |
| 52 | CH | S | CH | CH | N—CH₃ | — | — | 2.5 | 0.5 |
| 55 | N | S | CH | CH | N—CH₃ | 2.5 | — | 10 | 0.5 |
| 56 | CH | S | CH | CH | N—CH—C₂H₅<br>\|<br>CH₃ | — | — | 10 | 0.5 |
| 58 | N | S | CH | CH | N—i.C₃H₇ | — | 0.5 | 2.5 | 0.125 |
| 59 | CH | S | CH | CH | N—i.C₃H₇ | — | — | 10 | 0.5 |
| 201 | N | S | CH | N | N—CH₃ | — | — | 2.5 | 0.5 |
| 167 | N | S | CHOCH₃ | CH₂ | N—CH₂C₆H₅ | — | 0.5 | 2.5 | — |
| 166 | CH | S | CHOCH₃ | CH₂ | N—C₂H₅ | — | 0.5 | 0.63 | 0.125 |
| 169 | N | S | CHOCH₃ | CH₂ | N—CH₃ | 2.5 | 0.25 | 1.25 | 0.125 |
| 170 | CH | S | CHOCH₃ | CH₂ | N—CH(CH₃)C₂H₅ | 2.5 | — /1-butanol (1:1) | 2.5 | 0.125 |
| 139 | N | S | CH₂ | CH₂ | N—C₆H₅ | 2.5 | — | 2.5 | 0.125 |
| 179 | N | O | CH₂ | CH₂ | N—C₆H₅ | — | 0.5 | 2.5 | 0.125 |
| 171 | N | S | CHOCH₃ | CH₂ | N—C₂H₅ | — | 0.125 | ≦0.63 | 0.125 |
| 173 | N | S | CHOCH₃ | CH₂ | N—i.C₃H₇ | 2.5 | 0.125 | ≦0.63 | 0.125 |
| 164 | N | S | CH₂—CH₂—CH₂ | CH₂ | N—C₂H₅ | — | 1.25 | — | — |
| 159 | N | S | CH₂—CH₂—CH₂ | CH₂ | N—C₂H₅ | — | 0.5 | 2.5 | 0.5 |
| 160 | CH | S | CH₂—CH₂—CH₂ | CH₂ | N—C₂H₅ | — | — | 2.5 | 0.5 |
| 174 | CH | S | CHOCH₃ | CH₂ | N—i.C₃H₇ | — | 0.5 | ≦2.5 | ≦1.25 |
| 140 | CH | S | CH₂ | CH₂ | N—C₆H₅ | — | — | ≦2.5 | ≦0.125 |

TABLE II

| Comp. No. | Q | X | B | A | R¹ | Vaginal candidosis in rats Lowest oral dose in mg/kg | Vaginal candidosis in rats Lowest topical concentration (%) | Microsporum canis infection Lowest oral dose in mg/kg | Microsporum canis infection Lowest topical concentration (%) |
|---|---|---|---|---|---|---|---|---|---|
| 60 | CH | O | C=O | CH₂ | C₂H₅ | 2.5 | 0.1 | 5 | 0.5 |
| 6 | N | O | C=O | CH₂ | CH₃ | 2.5 | 0.05 | — | — |
| 5 | N | O | C=O | CH₂ | i.C₃H₇ | 1.25 | 0.05 | 10 | 0.25 |
| 25 | CH | O | C=O | CH₂ | C₃H₇ | 1.25 | 0.05 | 5 | 0.25 |
| 7 | CH | O | C=O | CH₂ | CH₃ | — | 0.06 | — | — |
| 8 | N | O | C=O | CH₂ | n.C₄H₉ | 0.31 | 0.06 | 10 | 0.125 |
| 9 | N | O | C=O | CH₂ | n.C₃H₇ | 1.25 | 0.03 | 5 | 0.125 |
| 10 | CH | O | C=O | CH₂ | n.C₃H₇ | 0.63 | 0.06 | 1.25 | 0.25 |
| 11 | N | O | C=O | CH₂ | C₂H₅ | 2.5 | 0.03 | — | 0.25 |
| 12 | CH | O | C=O | CH₂ | n.C₄H₉ | 2.5 | 0.1 | 5 | 0.5 |
| 152 | N | O | CH₂ | CH₂ | n.C₃H₇(CH₃)CH | 1.25 | 0.031 | 2.5 | 0.125 |
| 29 | CH | O | CH₂ | C=O | i.C₃H₇ | — | 0.125 | 1.25 | 0.25 |
| 30 | N | O | CH₂ | C=O | n.C₄H₉ | — | 0.5 | 0.31 | 0.1 |
| 31 | CH | O | CH₂ | C=O | C₂H₅ | 2.5 | 0.25 | 1.25 | 0.25 |
| 32 | N | O | CH₂ | C=O | C₂H₅ | — | 0.5 | — | 0.1 |
| 33 | N | O | CH₂ | C=O | n.C₃H₇ | 2.5 | — | — | 0.25 |
| 34 | CH | O | CH₂ | C=O | n.C₃H₇ | — | — | — | 0.25 |
| 26 | N | O | CH₂ | C=O | CH₃ | — | — | — | 0.25 |
| 27 | CH | O | CH₂ | C=O | CH₃ | 0.16 | 0.125 | 1.25 | 0.5 |
| 36 | N | O | CH₂ | CH₂ | C₂H₅ | 1.25 | <0.5 | 1.25 | 0.1 |
| 37 | CH | O | CH₂ | CH₂ | C₂H₅ | — | 0.125 | 1.25 | 0.06 |
| 156 | CH | S | CH₂ | CH₂ | i.C₄H₉ | 2.5 | — | <<10 | 0.25 |
| 38 | CH | O | CH₂ | CH₂ | n.C₄H₉ | 2.5 | 0.5 | 1.25 | 0.1 |
| 154 | CH | S | CH₂ | CH₂ | C₂H₅(CH₃)CH | — | 0.5 | — | 0.25 |
| 39 | N | O | CH₂ | CH₂ | n.C₃H₇ | 1.25 | 0.03 | 0.5 | 0.06 |
| 40 | CH | O | CH₂ | CH₂ | n.C₃H₇ | 2.5 | 0.125 | 1.25 | 0.5 |
| 41 | CH | O | CH₂ | CH₂ | i.C₃H₇ | 2.5 | 0.5 | 1.25 | 0.25 |
| 42 | N | O | CH₂ | CH₂ | i.C₃H₇ | 2.5 | 0.06 | <0.63 | 0.125 |
| 13 | N | O | C=O | CH₃CH | H | — | <0.125 | 10 | — |
| 14 | N | O | C=O | (CH₃)₂C | H | — | 0.25 | 5 | 0.5 |
| 35 | N | O | CH₂ | CH₂ | CH₃ | — | ≦0.125 | <10 | <0.5 |
| 43 | CH | O | CH₂ | CH₂ | CH₃ | <<2.5 | ≦0.125 | 2.5 | 0.5 |
| 44 | N | O | CH₂ | CH₂ | n.C₄H₉ | — | 0.1 | 2.5 | 0.06 |

| Comp. No. | Q | X | B | A | Z | Vaginal candidosis in rats Lowest oral dose in mg/kg | Vaginal candidosis in rats Lowest topical concentration (%) | Microsporum canis infection Lowest oral dose in mg/kg | Microsporum canis infection Lowest topical concentration (%) |
|---|---|---|---|---|---|---|---|---|---|
| 111 | N | O | CO | N—i.C₃H₇ | N—n.C₃H₇ | — | 0.5 | — | 0.5 |
| 112 | N | O | CO | N—n.C₄H₉ | N—n.C₄H₉ | 2.5 | 0.5 | — | — |
| 113 | CH | O | CO | N—CH₃ | N—CH₃ | 2.5 | — | 10 | — |
| 68 | CH | O | CO | CH(CH₃) | N—CH₃ | — | 0.125 | 10 | — |
| 69 | N | O | CO | C(CH₃)₂ | N—C₂H₅ | 2.5 | 0.125 | 2.5 | — |
| 70 | N | O | CO | C(CH₃)₂ | N—i.C₃H₇ | 2.5 | 0.063 | 1.25 | 0.125 |
| 71 | N | O | CO | C(CH₃)₂ | N—CH₃ | 2.5 | 0.063 | 2.5 | 0.5 |
| 73 | N | O | CO | C(CH₃)₂ | N—n.C₄H₉ | 1.25 | — | — | — |
| 3 | CH | O | CO | C(CH₃)₂ | NH | 2.5 | 0.5 | 2.5 | 0.5 |
| 74 | CH | O | CO | C(CH₃)₂ | N—CH₃ | 2.5 | 0.5 | 2.5 | 0.5 |
| 75 | CH | O | CO | C(CH₃)₂ | N—C₂H₅ | — | 0.5 | 2.5 | 0.5 |
| 76 | CH | O | CO | C(CH₃)₂ | N—n.C₃H₇ | 2.5 | 0.5 | 2.5 | 0.125 |
| 77 | CH | O | CO | C(CH₃)₂ | N—i.C₃H₇ | — | 0.5 | 2.5 | 0.125 |
| 78 | CH | O | CO | C(CH₃)₂ | N—n.C₃H₉ | — | 0.5 | 2.5 | 0.125 |
| 163 | CH | S | CH₂—CH₂—CH₂ | | N—C₂H₅ | — | 0.5 | ≦10 | — |
| 200 | CH | O | CO | CO | N—n.C₄H₉ | — | — | 10 | 0.5 |

TABLE II-continued

| Comp. No. | Q | X | B | A | | | Vaginal candidosis in rats Lowest oral dose in mg/kg | Vaginal candidosis in rats Lowest topical concentration (%) | Microsporum canis infection Lowest oral dose in mg/kg | Microsporum canis infection Lowest topical concentration (%) |
|---|---|---|---|---|---|---|---|---|---|---|
| 199 | CH | O | CO | CO | | N—i.C$_3$H$_7$ | — | — | ≦10 | 0.5 |
| 183 | N | O | CO | CO | | N—CH$_3$ | — | — | 10 | 0.5 |
| 184 | N | O | CO | CO | | N—C$_2$H$_5$ | 2.5 | 0.5 | 10 | 0.5 |
| 15 | N | O | CO | CH(CH$_3$) | | O | — | 0.5 | 10 | 0.5 |
| 16 | N | O | CO | C—(CH$_3$)$_2$ | | O | — | ≦1.25 | — | 0.5 |
| 185 | N | O | CO | CO | | N—n.C$_3$H$_7$ | — | 0.5 | 10 | 0.5 |
| 186 | N | O | CO | CO | | N—i.C$_3$H$_7$ | — | — | ≦2.5 | ≦0.125 |
| 79 | CH | O | CO | C(CH$_3$)$_2$ | | N—(CH$_2$)O—C$_2$H$_5$ | — | 0.5 | ≦2.5 | ≦0.125 |
| 80 | CH | O | CO | C(CH$_3$)$_2$ | | N—(CH$_2$)$_2$—OCH$_3$ | — | 0.5 | ≦2.5 | 0.5 |
| 181 | N | O | CO | CO | | N—n.C$_4$H$_9$ | — | — | 10 | 0.5 |
| 187 | CH | O | CO | CO | | N—i.C$_4$H$_9$ | — | 0.5 | 10 | — |
| 81 | CH | O | CO | C(CH$_3$)$_2$ | | N—(CH$_2$)O—C$_3$H$_7$ | — | 0.5 | — | 0.5 |
| 189 | N | O | CO | CO | | N—n.C$_5$H$_{11}$ | — | — | ≦10 | — |
| 82 | CH | O | CO | C(CH$_3$)$_2$ | | N—(CH$_2$)$_2$O—i.C$_3$H$_7$ | — | — | ≦10 | ≦0.5 |
| 83 | CH | O | CO | C(CH$_3$)$_2$ | | N—i.C$_4$H$_9$ | — | ≦0.5 | ≦10 | — |
| 17 | CH | O | CO | C(CH$_3$)$_2$ | | O | — | — | ≦10 | ≦0.5 |
| 190 | CH | O | CO | CO | | N—n.C$_3$H$_7$ | — | — | ≦10 | ≦0.5 |
| 84 | CH | O | CO | C(CH$_3$)$_2$ | | N—n.C$_5$H$_{11}$ | — | >0.5 | ≦10 | ≦0.5 |
| 85 | N | O | CO | C(CH$_3$)$_2$ | | N—CH$_2$OCH$_3$ | ≦2.5 | ≦0.5 | ≦10 | ≦0.5 |
| 191 | N | O | CO | CO | | N—i.C$_5$H$_{11}$ | — | — | — | ≦0.5 |
| 19 | CH | O | CO | CH(CH$_3$) | | O | — | ≦0.5 | ≦10 | ≦0.5 |
| 86 | CH | O | CO | C(CH$_3$)$_2$ | | N—CH(CH$_3$)—C$_2$H$_5$ | — | ≦0.5 | ≦10 | ≦0.5 |
| 87 | CH | O | CO | C(CH$_3$)$_2$ | | N—CH(CH$_3$)—C$_3$H$_7$ | — | ≦0.5 | ≦10 | ≦0.5 |
| 88 | CH | O | CO | C(CH$_3$)$_2$ | | N—i.C$_5$H$_{11}$ | — | — | ≦10 | ≦0.5 |
| 89 | CH | O | CO | C(CH$_3$)$_2$ | | N—CH$_2$—cyclopropyl | — | ≦0.5 | ≦10 | ≦0.5 |
| 92 | CH | O | CO | C(CH$_3$)$_2$ | | NCH$_2$CH=CH$_2$ | — | ≦0.5 | ≦10 | ≦0.5 |
| 192 | CH | O | CO | CO | | N—i.C$_5$H$_{11}$ | — | — | ≦10 | ≦0.5 |
| 193 | CH | O | CO | CO | | N—t.C$_4$H$_9$ | — | — | ≦10 | ≦0.5 |
| 94 | N | O | CO | C(CH$_3$)$_2$ | | N—(CH$_2$)$_2$—OC$_2$H$_5$ | — | ≦0.5 | ≦10 | — |
| 91 | N | O | CO | C(CH$_3$)$_2$ | | N—(CH$_2$)$_2$—O—i.C$_3$H$_7$ | ≦2.5 | ≦0.5 | ≦10 | ≦0.5 |

| | | | | | R$^1$ | R', R'' | | | | |
|---|---|---|---|---|---|---|---|---|---|---|
| 194 | CH | O | CO | CO | —CH(CH$_3$)—C$_2$H$_5$ | 2,4-Cl$_2$ | — | — | ≦10 | — |
| 195 | CH | O | CO | CO | n.C$_5$H$_{11}$ | 2,4-Cl$_2$ | — | — | ≦10 | ≦0.5 |
| 45 | N | O | CH$_2$ | CH$_2$ | n.C$_3$H$_7$ | 4-Cl | 1.25 | 0.031 | 1.25 | 0.125 |
| 46 | N | O | CH$_2$ | CH$_2$ | n.C$_3$H$_7$ | 2-Br,4-Cl | 2.5 | 0.125 | 0.63 | ≦0.125 |
| 47 | CH | O | CH$_2$ | CH$_2$ | n.C$_3$H$_7$ | 4-F | — | 0.5 | — | 0.5 |
| 48 | N | O | CH$_2$ | CH$_2$ | n.C$_3$H$_7$ | 2-Cl | — | ≦0.125 | 2.5 | 0.5 |
| 49 | N | O | CH$_2$ | CH$_2$ | n.C$_3$H$_7$ | 4-Br | — | 0.125 | 2.5 | 0.5 |

TABLE II-continued

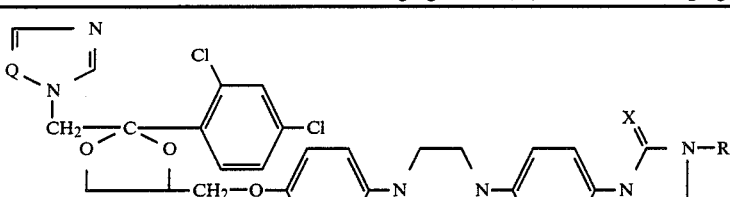

| Comp. No. | Q | X | B | A | R¹ | | Vaginal candidosis in rats Lowest oral dose in mg/kg | Vaginal candidosis in rats Lowest topical concentration (%) | Microsporum canis infection Lowest oral dose in mg/kg | Microsporum canis infection Lowest topical concentration (%) |
|---|---|---|---|---|---|---|---|---|---|---|
| 106 | CH | O | C=O | N—$C_2H_5$ | $C_2H_5$ | | — | 0.5 | 2.5 | 0.25 |
| 107 | CH | O | C=O | N—n.$C_3H_7$ | n.$C_3H_7$ | | 1.25 | 0.25 | 2.5 | 0.5 |
| 108 | N | O | C=O | N—$C_2H_5$ | $C_2H_5$ | | 2.5 | 0.06 | 10 | 0.25 |
| 109 | N | O | C=O | N—$CH_3$ | $CH_3$ | | 2.5 | 0.1 | — | 0.25 |
| 110 | CH | O | C=O | N—n.$C_4H_9$ | n.$C_4H_9$ | | 2.5 | 0.5 | 2.5 | 0.5 |
| 111 | N | O | C=O | N—n.$C_3H_7$ | n.$C_3H_7$ | | 2.5 | 0.125 | 10 | 0.25 |
| 112 | N | O | C=O | N—n.$C_4H_9$ | n.$C_4H_9$ | | 1.25 | 0.25 | — | — |
| 113 | CH | O | C=O | N—$CH_3$ | $CH_3$ | | 1.25 | 0.5 | 5 | 0.5 |

TABLE III $r_a$ is hydrogen where not otherwise indicated.

| Int. No. | Q | X | $Z^1$ | $R^7$ | Vaginal candidosis in rats Lowest oral dose in mg/kg | Vaginal candidosis in rats Lowest topical concentration (%) | Microsporum canis infection Lowest oral dose in mg/kg | Microsporum canis infection Lowest topical concentration (%) |
|---|---|---|---|---|---|---|---|---|
| 152 | CH | O | O | $CH_3$ | 1.0 | <0.5 | ≦10 | ≦0.25 |
| 153 | CH | O | O | $C_2H_5$ | — | — | — | ≦0.05 |
| 156 | CH | S | NH | $CH_3$ | 2.5 | — | — | — |
| 158 | CH | O | NH | $CH_3$ | 2.5 | — | — | — |
| 154 | N | O | O | $C_2H_5$ | 2.5 | — | — | — |
| 2 | CH | O | O | $C_6H_5$ | 2.5 | — | — | — |
| 155 | N | O | O | $CH_3$ | <0.63 | <0.125 | — | ≦0.5 |
| 1 | N | O | O | $C_6H_5$ | 2.5 | — | — | ~0.5 |
| 159 | N | O | NH | $CH_3$ | 2.5 | — | — | ≧0.5 |
| 160 | N | O | NH | $C_2H_5$ | — | — | <10 | ~0.5 |
| 161 | CH | O | NH | $C_2H_5$ | 2.5 | — | 5 | — |
| 157 | CH | O | NH | n.$C_3H_7$ | 2.5 | <0.125 | ~10 | ≦0.5 |
| 162 | N | O | NH | n.$C_3H_7$ | — | <0.125 | ~5 | ≦0.5 |
| 106 | N | O | NH | $(CH_3O)_2CH$—$CH_2$ | — | <0.5 | <10 | — |
| 86 | CH | O | N—$C_2H_5$ | $CH_2CH_2OH$ | — | ≦0.5 | 5 | ~0.5 |
| 87 | N | O | N—$C_2H_5$ | $CH_2CH_2OH$ | — | ~0.125 | ~10 | — |
| 85 | N | O | N—$CH_3$ | $CH_2CH_2OH$ | — | — | — | ~0.5 |
| 100 | CH | O | N—n.$C_4H_9$ | $CH_2CH_2OH$ | 2.5 | 0.2 | 1.25 | 0.4 |
| 101 | CH | O | N—n.$C_3H_7$ | $CH_2CH_2OH$ | — | 0.25 | 5 | 0.25 |
| 88 | N | O | N—n.$C_3H_7$ | $CH_2CH_2OH$ | — | 0.125 | 5 | — |
| 89 | N | O | N—n.$C_4H_9$ | $CH_2CH_2OH$ | — | 0.25 | 1.25 | 0.25 |
| 90 | N | O | N—i.$C_3H_7$ | $CH_2CH_2OH$ | — | 0.25 | 10 | — |
| 91 | N | O | N—$CH(CH_3)C_2H_5$ | $CH_2CH_2OH$ | — | 0.25 | — | — |
| 92 | N | O | N—i.$C_4H_9$ | $CH_2CH_2OH$ | — | 0.125 | 5 | — |
| 93 | N | O | N—i.$C_5H_{11}$ | $CH_2CH_2OH$ | 2.5 | 0.125 | 5 | ~0.5 |
| 94 | N | O | N—$CH_2CHC_2H_5$ \| $CH_3$ | $CH_2CH_2OH$ | — | 0.063 | 10 | 0.25 |
| 95 | N | O | N—$CH(C_2H_5)_2$ | $CH_2CH_2OH$ | — | <0.5 | — | ~0.5 |
| 98 | N | O | N—n.$C_5H_{11}$ | $CH_2CH_2OH$ | 2.5 | 0.125 | 1.25 | 0.25 |

TABLE III-continued

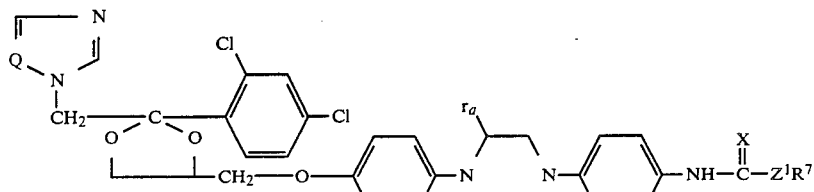

$r_a$ is hydrogen where not otherwise indicated.

| Int. No. | Q | X | $Z^1$ | $R^7$ | Vaginal candidosis in rats Lowest oral dose in mg/kg | Vaginal candidosis in rats Lowest topical concentration (%) | Microsporum canis infection Lowest oral dose in mg/kg | Microsporum canis infection Lowest topical concentration (%) |
|---|---|---|---|---|---|---|---|---|
| 96 | N | O | $N-CH(CH_3)n.C_3H_7$ | $CH_2CH_2OH$ | $\geqq 2.5$ | 0.125 | 5 | 0.25 |
| 110 | CH | S | $N-CH(CH_3)C_2H_5$ | $CH_2CH_2OH$ | — | $\leqq 0.125$ | 5 | ~0.5 |
| 109 | CH | S | $N-C_2H_5$ | $CH_2CH_2OH$ | 2.5 | 0.125 | 1.25 | 0.25 |
| 112 | CH | S | $N-i.C_3H_7$ | $CH_2CH_2OH$ | — | 0.125 | 2.5 | — |
| 113 | CH | S | $N-n.C_3H_7$ | $CH_2CH_2OH$ | — | $\leqq 0.125$ | 1.25 | 0.5 |
| 3 | N | O | O | $C_6H_5$ $r_a = CH_3$ | — | — | ~10 | 0.5 |
| 111 | CH | S | $N-i.C_5H_{11}$ | $CH_2CH_2OH$ | ~2.5 | 0.5 | 5 | $\geqq 0.5$ |
| 115 | N | S | $N-C_2H_5$ | $CH_2CH_2OH$ | >2.5 | 0.25 | 2.5 | 0.25 |
| 116 | N | S | $N-CH(CH_3)C_2H_5$ | $CH_2CH_2OH$ | 1.25 | $\leqq 0.125$ | 5 | ~0.5 |
| 117 | CH | S | $N-n.C_4H_9$ | $CH_2CH_2OH$ | 2.5 | $\geqq 0.5$ | 5 | 0.25 |
| 118 | N | S | $N-n.C_3H_7$ | $CH_2CH_2OH$ | — | 0.25 | 1.25 | 0.25 |
| 103 | N | O | $N-C_2H_5$ | $CH_2CH_2OH$ | 2.5 | 0.5 | — | — |
| 120 | CH | S | $N-CH_3$ | $CH_2CH_2OH$ | — | $\leqq 0.5$ | — | — |
| 121 | N | S | $N-n.C_5H_{11}$ | $CH_2CH_2OH$ | — | $\leqq 0.125$ | 2.5 | — |
| 123 | CH | S | $N-n.C_5H_{11}$ | $CH_2CH_2OH$ | — | <0.5 | 5 | 0.5 |
| 124 | N | S | $N-CH_3$ | $CH_2CH_2OH$ | — | 0.125 | $\geqq 10$ | $\geqq 0.5$ |
| 125 | CH | S | $N-CH(C_2H_5)_2$ | $CH_2CH_2OH$ | — | >0.5 | 5 | ~0.5 |
| 127 | N | S | $N-CH(C_2H_5)_2$ | $CH_2CH_2OH$ | 5 | 0.25 | 5 | ~0.5 |
| 128 | N | S | $N-n.C_4H_9$ | $CH_2CH_2OH$ | <10 | 0.25 | <10 | <0.5 |
| 142 | N | S | $N-CH_2C_6H_5$ | $CH_2CH(OCH_3)_2$ | — | 0.5 | 10 | 0.5 |
| 143 | CH | S | $N-C_2H_5$ | $CH_2CH(OCH_3)_2$ | — | 0.5 | 2.5 | 0.5 |
| 141 | CH | S | $N-CH_3$ | $CH_2CH(OCH_3)_2$ | — | 0.5 | 2.5 | 0.125 |
| 140 | N | S | $N-C_2H_5$ | $(CH_2)_2NHC_2H_5$ | — | 0.5 | 10 | — |
| 144 | CH | S | $N-CH-C_2H_5$ \| $CH_3$ | $CH_2CH(OCH_3)_2$ | — | 0.5 | 10 | 0.5 |
| 145 | N | S | $N-CH_3$ | $CH_2CH(OCH_3)_2$ | — | 0.5 | 2.5 | 0.5 |
| 146 | N | S | $N-C_2H_5$ | $CH_2CH(OCH_3)_2$ | 2.5 | 0.25 | 1.25 | 0.125 |
| 147 | CH | S | $N-i.C_3H_7$ | $CH_2CH(OCH_3)_2$ | — | 0.5 | — | 0.5 |
| 149 | N | S | $N-i.C_3H_7$ | $CH_2CH(OCH_3)_2$ | — | 0.5 | 2.5 | 0.5 |
| 133 | CH | S | $N-C_2H_3$ | $(CH_2)_3OH$ | — | — | 2.5 | — |
| 182 | CH | O | $N-i.C_3H_7$ | H | — | 0.5 | 2.5 | — |
| 134 | N | S | $N-i.C_4H_9$ | $(CH_2)_3OH$ | — | 0.5 | 10 | 0.5 |
| 135 | CH | S | $N-i.C_4H_9$ | $(CH_2)_3OH$ | 2.5 | — | 10 | — |
| 181 | N | O | $N-i.C_3H_7$ | H | 2.5 | $\leqq 1.25$ | $\leqq 2.5$ | 0.5 |
| 179 | CH | O | $N-i.C_4H_9$ | H | — | $\leqq 0.5$ | $\leqq 10$ | — |
| 177 | N | O | $N-i.C_4H_9$ | H | — | $\leqq 0.125$ | — | — |
| 175 | N | O | $N-i.C_5H_{11}$ | H | — | — | — | $\leqq 0.5$ |
| 174 | N | O | $N-CHC_2H_5$ \| $CH_3$ | H | — | — | — | $\leqq 0.5$ |
| 173 | CH | O | $N-t.C_4H_9$ | H | 2.5 | — | — | $\leqq 0.5$ |
| 172 | CH | O | $N-n.C_5H_{11}$ | H | — | — | — | $\leqq 0.5$ |
| 171 | CH | O | $N-i.C_5H_{11}$ | H | $\leqq 2.5$ | — | — | $\leqq 0.5$ |
| 169 | CH | O | $N-(4-CH_3-C_6H_4)$ | H | — | — | $\leqq 10$ | — |

In view of their antifungal and antibacterial properties this invention provides valuable compositions comprising the compounds of formula (I), (XII-a-1), acid addition salts or stereochemically isomeric forms thereof, as the active ingredient in a solvent or a solid, semi-solid or liquid diluent or carrier, and, in addition, it provides an effective method of combatting fungal or bacterial growth by use of an effective antifungal or antibacterial amount of such compound (I), (XII-a-1) or salts thereof. Antifungal and anti-bacterial compositions comprising an effective amount of an active compound (I) or (XII-a-1), either alone or in combination with other active therapeutic ingredients, in admixture with suitable carriers may be readily prepared according to conventional pharmaceutical techniques for the usual routes of administration.

Preferred compositions are in dosage unit form, comprising per dosage unit an effective quantity of the active ingredient in admixture with suitable carriers. Although the amount of the active ingredient per unit dosage may vary within rather wide limits, dosage units comprising from about 1 to about 500 mg and more particularly from about 10 to about 250 mg of the active ingredient are preferred.

To prepare the pharmaceutical compositions of this invention an antimicrobially effective amount of the particular compound or compounds, in base or acid-addition salt form, as the active ingredients, is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof. The amount of active ingredient per dosage unit is from about 0.25 mg to about 100 mg and, preferably from about 0.5 to about 20 mg.

The following formulations exemplify compositions typical for the treatment of vaginal candidosis in dosage unit form suitable for systemic or topical administration to animal and human subjects in accordance with the instant invention.

Oral drops: The following formulation provides 50 liters of an oral-drop solution comprising 10 milligrams of cis-1-butyl-3-[4-[4-[4-[[2-(2,4-dichlorophenyl)-2-(1H-1,2,4-triazol-1-ylmethyl)-1,3-dioxolan-4-yl]metho xy]-phenyl]-1-piperazinyl]phenyl]-2,4-imidazolidinedione (A.I.) per milliliter.

| A.I. | 500 grams |
| 2-hydroxypropanoic acid | 0.5 liter |
| Sodium saccharin | 1750 grams |
| Cocoa flavor | 2.5 liters |
| Purified water | 2.5 liters |
| Polyethylene glycol q.s. ad | 50 liters |

The A.I. was dissolved in the 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of the sodium saccharin in 2.5 liters of purified water and while stirring there were added the cocoa flavor and polyethylene glycol q.s. ad volume. The resulting solution was filled into suitable containers.

Injectable solution: The following formulation provides 20 liters of a parenteral solution comprising 2 milligrams of cis-1-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl ]-3-propyl-2-imidazolidinone per milliliter.

| A.I. | 40 grams |
| 2,3-dihydroxybutanedioic acid | 20 grams |
| methyl 4-hydroxybenzoate | 36 grams |
| propyl 4-hydroxybenzoate | 4 grams |
| water for injection q.s. ad | 20 liters. |

The methyl and propyl 4-hydroxybenzoates were dissolved in about 10 liters of boiling water for injection. After cooling to about 50° C. there were added while stirring the 2,3-dihydroxy butanedioic acid and thereafter the A.I.. The solution was cooled to room temperature and supplemented with water for injection q.s. ad volume. The solution was sterilized by filtration (U.S.P. XVII p. 811) and filled in sterile containers.

Oral solution: The following formulation provides 20 liters of an oral solution comprising 5 milligrams of cis-1-[4-[4-[4-[[2-(2,4-dichlorophenyl)-2-(1H-1,2,4-triazol-1-ylmethyl)-1,3-dioxolan-4-yl]methoxy]phenyl]-1 1-piperazinyl]phenyl]-3-propyl-2-imidazolidinone per teaspoonful (5 milliliters).

| A.I. | 20 grams |
| 2,3-dihydroxybutanedioic acid | 10 grams |
| Sodium saccharin | 40 grams |
| 1,2,3-propanetriol | 12 liters |
| Sorbitol 70% solution | 3 liters |
| Methyl 4-hydroxybenzoate | 9 grams |
| Propyl 4-hydroxybenzoate | 1 gram |
| Raspberry essence | 2 milliliters |
| Gooseberry essence | 2 milliliters |
| Purified water q.s. ad | 20 liters. |

The methyl and propyl 4-hydroxybenzoates were dissolved in 4 liters of boiling purified water. In 3 liters of this solution were dissolved first the 2,3-dihydroxybutanedioic acid and thereafter the A.I.. The latter solution was combined with the remaining part of the former solution and the 1,2,3-propanetriol and the sorbitol solution were added thereto. The sodium saccharin was dissolved in 0.5 liters of water and the raspberry and gooseberry essences were added. The latter solution was combined with the former, water was added q.s. ad volume and the resulting solution was filled in suitable containers.

Film-coated tablets: 10,000 Compressed tablets, each containing as the active ingredient 10 milligrams of cis-1-butyl-3-[4-[4-[4-[[2-(2,4-dichlorophenyl)-2-(1H-1,2,4-triazol-1-ylmethyl)-1,3-dioxolan-4-yl]methoxy]- phe nyl]-1-piperazinyl]phenyl]-2,4-imidazolidinedione were prepared from the following formulation:

| Tablet core: | |
|---|---|
| A.I. | 100 grams |
| Lactose | 570 grams |
| Starch | 200 grams |
| Polyvinylpyrrolidone (Kollidon K90) | 10 grams |
| Microcrystalline cellulose (Avicel) | 100 grams |
| Sodium dodecyl sulfate | 5 grams |
| Hydrogenated vegetable oil (Sterotex) | 15 grams |
| Coating: | |
| Methyl cellulose (Methocel 60 HG) | 10 grams |
| Ethyl cellulose (Ethocel 22 cps) | 5 grams |
| 1,2,3-propanetriol | 2.5 milliliters |
| Polyethylene glycol 6000 | 10 grams |
| Concentrated colour suspension (Opaspray K-1-2109) | 30 milliliters |
| Polyvinylpyrrolidone (Povidone) | 5 grams |
| Magnesium octadecanoate | 2.5 grams |

Preparation of tablet core

A mixture of the A.I., the lactose and the starch was mixed well and thereafter humidified with a solution of the sodium dodecyl sulfate and the polyvinylpyrrolidone in about 200 milliliters of water. The wet powder was sieved, dried and sieved again. Then there was added the microcrystalline cellulose and the hydrogenated vegetable oil. The whole was mixed well and compressed into tablets.

Coating

To a solution of the methyl cellulose in 75 milliliters of denaturated ethanol there was added a solution of the ethyl cellulose in 150 milliliters of dichloromethane. Then there were added 75 milliliters of dichloromethane and 1,2,3-propanetriol. The polyethylene glycol was molten and dissolved in 75 milliliters of dichloromethane. The latter solution was added to the former and than there were added the magnesium octadecanoate, the polyvinylpyrrolidone and the concentrated colour suspension and the whole was homogenized.

The tablet cores were coated with the thus obtained mixture in a coating apparatus.

Suppositories: Hundred suppositories each containing 3 milligrams cis-1-butyl-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4 -imidazolidinedione were prepared from the following formulations:

| A.I. | 0.3 grams |
|---|---|
| 2,3-dihydroxybutanedioic acid | 3 grams |
| Polyethylene glycol 400 | 25 milliliters |
| Surfactant (Span) | 12 grams |
| Triglycerides (Witepsol 555) q.s. ad | 300 grams. |

The A.I. was dissolved in a solution of the 2,3-dihydroxybutanedioic acid in polyethylene glycol 400. The surfactant and the triglycerides were molten together. The latter mixture was mixed well with the former solution. The thus obtained mixture was poured onto moulds at a temperature of 37°–38° C. to form the suppositories.

In view of the antimicrobial properties of the compounds of formula (I) or (XII-a-1), it is evident that the present invention provides a method of inhibiting and/or eliminating the development of fungi and bacteria in warm-blooded animals suffering from diseases caused by these fungi and/or bacteria by the systemic or topical administration of an antimicrobially effective amount of a compound of formula (I), (XII-a-1), pharmaceutically acceptable acid addition salt or a stereochemically isomeric form thereof.

The following examples are intended to illustrate and not to limit the scope of the present invention. Unless otherwise stated all parts therein are by weight.

EXAMPLES

A. Preparation of Intermediates

EXAMPLE I

To a stirred solution of 13.5 parts of phenyl carbonochloridate in 100 parts of pyridine and 390 parts of dichloromethane were added dropwise 47 parts of cis-4-[4-[4-[2-(2,4-dichlorophenyl)-2-(1H-1,2,4-triazol-1-ylmethyl)-1,3-dioxolan-4-ylmethoxy]phenyl]-1-piperazinyl]benzenamine. Upon completion, stirring was continued for 3 hours at room temperature. 200 Parts of water and 140 parts of petroleumether were added. The precipitated product was filtered off, washed successively with water, 2-propanol, 2,2'-oxybispropane and dichloromethane, and dried, yielding 49 parts (86%) of cis-phenyl [4-[4-[4-[2-(2,4-dichlorophenyl)-2-(1H-1,2,4-triazol-1-ylmethyl)-1,3-dioxolan-4-ylmethoxy]phenyl]-1-piperazinyl]phenyl]-carbamate; mp. 203.1° C. (1).

In a similar manner there were also prepared:
cis-phenyl [4-[4-[4-[2-(2,4-dichlorophenyl)-2-(1H-imidazol-1-ylmethyl)-1,3-dioxolan-4-ylmethoxy]-phenyl]-1-piperazinyl]phenyl]carbamate; mp. 198.8° C. (2);

phenyl cis-[4-[4-[4-[[2-(2,4-dichlorophenyl)-2-(1H-1,2,4-triazol-1-ylmethyl)-1,3-dioxolan-4-yl]methoxy]-phenyl]-3-methyl-1-piperazinyl]phenyl]car bamate; mp. 168.5° C. (3); and phenyl cis-[4-[4-[4-[[2-(4-chlorophenyl)-2-(1H-1,2,4-triazol-1-ylmethyl)-1,3-dioxolan-4-yl]methoxy]-phenyl]-1-piperazinyl]phenyl]carbamate; mp. 215.5° C. (4).

EXAMPLE II

To a stirred and cooled (ice-bath) mixture of 12.6 parts of carbon disulfide, 2.1 parts of N,N'-methanetetraylbis[cyclohexanamine] and 30 parts of pyridine were added 5.8 parts of cis-4-[4-[4-[2-(2,4-dichlorophenyl)-2-(1H-imidazol-1-ylmethyl)-1,3-dioxolan-4-ylmethoxy]-phenyl]-1-piperazinyl]benzenamine and stirring was continued first for 2 hours while cooling in an icebath and then for 1 hour at room temperature. 42 Parts of 2,2'-oxybispropane were added and the product was allowed to crystallize. It was filtered off and purified by filtration over silica gel using a mixture of trichloromethane and methanol (99:1 by volume) as eluent. The pure fractions were collected and the eluent was evaporated. The residue was crystallized from 4-methyl-2-pentanone, yielding 3.8 parts (61%) of cis-1-[4-[[2-(2,4-dichlorophenyl)-2-(-b 1H-imidazol-1-ylmethyl)-1,3-dioxolan-4-yl]methoxy]phenyl]-4-(4-isothiocyanatophenyl)piperazine; mp. 165.4° C. (5).

In a similar manner there were also prepared:
cis-1-[4-[[2-(2,4-dichlorophenyl)-2-(1H-1,2,4-triazol-1-ylmethyl)-1,3-dioxolan-4-yl]methoxy]phenyl]-4-(4-isothiocyanatophenyl)piperazine; mp. 149.1° C. (6).

EXAMPLE III

A mixture of 21 parts of 1-(4-nitrophenyl)-2-imidazolidinone, 16 parts of iodomethane, 10 parts of potassium hydroxide and 200 parts of dimethyl sulfoxide was stirred for 3 hours at room temperature. Another portion of 16 parts of iodomethane and 10 parts of potassium hydroxide were added. Stirring was continued overnight. 300 Parts of water were added to the reaction mixture and the whole was stirred. The precipitated product was filtered off and crystallized from 4-methyl-2-pentanone, yielding 16.5 parts (74%) of 1-methyl-3-(4-nitrophenyl)-2-imidazolidinone; mp. 214.1°–215.5° C. (7).

In a similar manner there were also prepared:
1-ethyl-3-(4-nitrophenyl)-2-imidazolidinone; mp. 175.2° C. (8);
1-(1-methylethyl)-3-(4-nitrophenyl)-2-imidazolidinone; mp. 161.7° C. (9);
1-butyl-3-(4-nitrophenyl)-2-imidazolidinone; mp. 130.0° C. (10); and
1-(4-nitrophenyl)-3-propyl-2-imidazolidinone; mp. 128.2° C. (11).

EXAMPLE IV

A mixture of 2.7 parts of ethyl 2-[(4-aminophenyl)amino]-acetate hydrochloride, 1.1 parts of acetic acid anhydride, 0.98 parts of sodium hydrogen carbonate, 65 parts of dichloromethane and 50 parts of water was stirred for 30 minutes at room temperature. The organic phase was separated, washed with water, dried, filtered and evaporated. The residue was crystallized from a mixture of 4-methyl-2-pentanone and 2,2'-oxybispropane, yielding 1.9 parts (68%) of ethyl 2-[[4-(acetylamino)phenyl]amino]acetate; mp. 119.5° C. (12).

EXAMPLE V

A mixture of 25 parts of ethyl 2-[[4-(acetylamino)phenyl]amino]acetate, 20 parts of 1-isocyanatobutane, 2 parts of N,N-dimethyl-4-pyridinamine and 300 parts of trichloromethane was stirred and refluxed for 48 hours. The reaction mixture was evaporated and the residue was stirred and refluxed for 8 hours in 180 parts of dimethylbenzene. After cooling, the precipitated product was filtered off, washed with 2-propanol and dried, yielding 25.5 parts (83%) of N-[4-(3-butyl-2,4-dioxo-1-imidazolidinyl)phenyl]acetamide; mp. 192.8° C. (13).

In a similar manner there were also prepared:
N-[4-(3-methyl-2,4-dioxo-1-imidazolidinyl)phenyl]acetamide; mp. 262.7° C.; (14)
N-[4-[3-(1-methylethyl)-2,4-dioxo-1-imidazolidinyl]phenyl]acetamide; mp. 215° C.; (15)
N-[4-(3-ethyl-2,4-dioxo-1-imidazolidinyl)phenyl]acetamide; mp. 250.5° C. (16) and
N-[4-(2,4-dioxo-3-propyl-1-imidazolidinyl)phenyl]acetamide; mp. 212.3° C. (17).

EXAMPLE VI

A mixture of 12 parts of 1-ethyl-3-(4-nitrophenyl)-2-imidazolidinone, 1 part of a solution of thiophene in ethanol 4% and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was crystallized from 2,2'-oxybispropane. The product was filtered off and dried, yielding 9.6 parts (93%) of 1-(4-aminophenyl)-3-ethyl-2-imidazolidinone (18).

In a similar manner there were also prepared:
1-(4-aminophenyl)-3-(1-methylethyl)-2-imidazolidinone (19);
1-(4-aminophenyl)-3-butyl-2-imidazolidinone (20);
1-(4-aminophenyl)-3-propyl-2-imidazolidinone (21); and
1-(4-aminophenyl)-3-methyl-2-imidazolidinone (22).

EXAMPLE VII

A mixture of 19.5 parts of N-[4-(2,4-dioxo-3-propyl-1-imidazolidinyl)phenyl]acetamide and 480 parts of concentrate hydrochloric acid was stirred and refluxed for 5 hours. The reaction mixture was cooled, the precipitated product was filtered off and dissolved in a mixture of methanol and water. The solution was neutralized with a sodium hydrogen carbonate solution and the product was extracted with trichloromethane. The extract was dried, filtered and evaporated, yielding 15 parts (90%) of 1-(4-aminophenyl)-3-propyl-2,4-imidazolidinedione; mp. 133.2° C. (23).

In a similar manner there were also prepared:
1-(4-aminophenyl)-3-(1-methylethyl)-2,4-imidazolidinedione; mp. 109.4° C. (24);
1-(4-aminophenyl)-3-methyl-2,4-imidazolidinedione; mp. 201.5° C. (25);
1-(4-aminophenyl)-3-ethyl-2,4-imidazolidinedione; mp. 149.3° C. (26); and
1-(4-aminophenyl-3-butyl-2,4-imidazolidinedione; mp. 114.8° C. (27).

EXAMPLE VIII

A mixture of 16.5 parts of N,N-bis(2-chloroethyl)-4-methoxybenzenamine, 12.5 parts of 1-(4-aminophenyl)-3-methyl-2-imidazolidinone, 11 parts of sodium hydrogen carbonate and 240 parts of 1-butanol was stirred and refluxed for 24 hours. After cooling, 100 parts of water were added and the whole was stirred. The precipitated product was filtered off, washed with water and with 1-butanol and dried, yielding 17.5 parts (73%) of 1-[4-[4-(4-methoxyphenyl)-1-piperazinyl]phenyl]-3-methyl-2-imidazolidinone; mp. 240.9°–241.0° C. (28).

In a similar manner there were also prepared:
1-[4-[4-(4-methoxyphenyl)-1-piperazinyl]phenyl]-3-(1-methylethyl)-2,4-imidazolidinedione; mp. 214.2° C. (29);
3-ethyl-1-[4-[4-(4-methoxyphenyl)-1-piperazinyl]phenyl]-2,4-imidazolidinedione; mp. 228.0° C. (30);
3-butyl-1-[4-[4-(4-methoxyphenyl)-1-piperazinyl]phenyl]-2,4-imidazolidinedione; mp. 206.7° C.; (31)
1-[4-[4-(4-methoxyphenyl)-1-piperazinyl]phenyl]-3-methyl-2,4-imidazolidinedione; mp. 258.7° C.; (32)
1-[4-[4-(4-methoxyphenyl)-1-piperazinyl]phenyl]-3-propyl-2,4-imidazolidinedione; mp. 200.8° C.; (33)
1-ethyl-3-[4-[4-(4-methoxyphenyl)-1-piperazinyl]phenyl]-2-imidazolidinedione; mp. 246.3° C.; (34)
1-[4-[4-(4-methoxyphenyl)-1-piperazinyl]phenyl]-3-(1-methylethyl)-2-imidazolidinone; mp. 234.5° C.; (35)
1-butyl-3-[4-[4-(4-methoxyphenyl)-1-piperazinyl]phenyl]-2-imidazolidinone; mp. 240.4° C.; (36) and
1-[4-[4-(4-methoxyphenyl)-1-piperazinyl]phenyl]-3-propyl-2-imidazolidinone; mp. 252.0° C. (37).

EXAMPLE IX

A mixture of 5 parts of phenyl [4-[4-(4-methoxyphenyl)-1-piperazinyl]phenyl]carbamate, 3 parts of ethyl [(1-methylethyl)amino]acetate, 1 part of N,N-dimethyl-4-pyridinamine and 100 parts of 1,4-dioxane was stirred and refluxed overnight. The warm solution was saturated with water and allowed to cool. The solution was poured onto water and extracted with trichloromethane. The extract was washed with water, dried, filtered and evaporated. The residue was purified by filtration over silica gel using a mixture of trichloromethane and methanol (98:2 by volume) as eluent. The filtrate was evaporated and the residue was crystallized from methylbenzene, yielding 3.7 parts (73%) of 3-[4-[4-(4-methoxyphenyl)-1-piperazinyl]phenyl]-1-(1-methylethyl)-2,4-imidazolidinedione; mp. 193.7° C. (38).

A mixture of 24 parts of phenyl [4-[4-(4-methoxyphenyl)-1-piperazinyl]phenyl]carbamate, 15.9 parts of ethyl N-butylglycine, 2 parts of N,N dimethyl-4-pyridinamine and 200 parts of 1,4-dioxane was stirred and refluxed overnight. Then water was added and stirring was continued for a while. The reaction mixture was cooled, poured onto water and the whole was stirred. The precipitated product was filtered off, washed with water and dissolved in 150 parts of trichloromethane. This solution was stirred for 30 minutes with 3 parts of silica gel. The latter was filtered off and the filtrate was evaporated. The residue was crystallized from butanol. The product was filtered off and dried in vacuo at 60° C., yielding 2.3 parts of 1-butyl-3-[4-[4-(4-methoxyphenyl)-1-piperazinyl]phenyl]-2,4-imidazolidinedione; mp. 183.7° C. (39).

EXAMPLE X

A mixture of 15 parts of 1-(4-isothiocyanatophenyl)-4-(4-methoxyphenyl)piperazine, 6.5 parts of 2,2-dimethoxy-N-methylethanamine and 195 parts of dichloromethane was stirred for 1 hour at room temperature. The reaction mixture was evaporated and the residue was triturated in 4-methyl-2-pentanone. The product was filtered off and dried, yielding 19.4 parts (95%) of N-(2,2-dimethoxyethyl)-N'-[4-[4-(4-methoxyphenyl)-1-piperazinyl]phenyl]-N-methylthiourea; mp. 155.0° C. (40).

In a similar manner there were also prepared:
N-(2,2-dimethoxyethyl)-N-ethyl-N'-[4-[4-(4-methoxyphenyl)-1-piperazinyl]phenyl]thiourea (41);
N-(2,2-dimethoxyethyl)-N'-[4-[4-(4-methoxyphenyl)-1-piperazinyl]-phenyl]-N-(1-methylethyl)thiourea; mp. 139.7° C. (42); and
N-(2,2-dimethoxyethyl)-N'-[4-[4-(4-methoxyphenyl)-1-piperazinyl]-phenyl]-N-(1-methylpropyl)thiourea; mp. 140° C. (43).

EXAMPLE XI a. A mixture of 10 parts of 1-(4-isothiocyanatophenyl)-4-(4-methoxyphenyl)piperazine, 6.3 parts of 3-(butylamino)-1-propanol and 130 parts of dichloromethane was stirred for 3 hours at room temperature. The reaction mixture was evaporated and the residue was triturated in 2-propanone. The product was filtered off and dried, yielding 12.7 parts (92%) of N-butyl-N-(3-hydroxypropyl)-N'-[4-[4-(4-methoxyphenyl)-1-piperazinyl]phenyl]thiourea; mp. 153.9° C. (44).

b. To 75 parts of a hydrobromic acid solution 48% in water was added a small amount of sodium hydrogen sulfite. Then there were added 1.7 parts of N-butyl-N-(3-hydroxypropyl)-N'-[4-[4-(4-methoxyphenyl)-1-piperazinyl]phenyl]thiourea. The whole was stirred and refluxed for 3 hours. The reaction mixture was evaporated. The residue was dissolved in a mixture of methanol and water. The solution was neutralized with a sodium hydrogen carbonate solution. The product was extracted with dichloromethane. The extract was washed with water, dried, filtered and evaporated. The residue was purified by column chromatography over silica gel using a mixture of trichloromethane and methanol (98:2 by volume) as eluent. The pure fractions were collected and the eluent was evaporated. The residue was crystallized from 2-propanol. The product was filtered off and dried, yielding 0.6 parts (38%) of 4-[4-[4-[(3-butyltetrahydro-1,3-thiazin-2-ylidene)amino]phenyl]-1-piperazinyl]phenol; mp. 143.0° C. (45).

EXAMPLE XII

A mixture of 7 parts of 1-[4-[4-(4-methoxyphenyl)-1-piperazinyl]-phenyl]-3-propyl-2-imidazolidinone and 225 parts of a hydrobromic acid solution 48% was stirred and refluxed for 5 hours. After cooling, the precipitated product was filtered off, washed with 2-propanol and dissolved in a mixture of methanol and water. The solution was neutralized with a sodium hydrogen carbonate solution. The product was extracted with trichloromethane. The extract was dried, filtered and evaporated. The residue was triturated in dichloromethane. The product was filtered off and dried, yielding 6 parts (89%) of 1-[4-[4-(4-hydroxyphenyl)-1-piperazinyl]phenyl]-3-propyl-2-imidazolidinone (46).

In a similar manner there were also prepared:
1-ethyl-3-[4-[4-(4-hydroxyphenyl)-1-piperazinyl]-phenyl]-2-imidazolidinone; mp. +300° C. (dec.); (47)
1-butyl-3-[4-[4-(4-hydroxyphenyl)-1-piperazinyl]-phenyl]-2-imidazolidinone; mp. 217.5° C.; (48)
1-[4-[4-(4-hydroxyphenyl)-1-piperazinyl]phenyl]-3-(1-methylethyl)-2-imidazolidinone; mp. 250.0° C. (49);
1-butyl-3-[4-[4-(4-hydroxyphenyl)-1-piperazinyl]-phenyl]-2,4-imidazolidinedione (50);
3-[4-[4-(4-hydroxyphenyl)-1-piperazinyl]phenyl]-1-(1-methylethyl)-2,4-imidazolidinedione; mp. 244.1° C. (51);
1-[4-[4-(4-hydroxyphenyl)-1-piperazinyl]phenyl]-3-propyl-2,4-imidazolidinedione; mp. 210.9° C. (52);
1-[4-[4-(4-hydroxyphenyl)-1-piperazinyl]phenyl]-3-(1-methylethyl)-2,4-imidazolidinedione; mp. 249° C.; (53)
3-ethyl-1-[4-[4-(4-hydroxyphenyl)-1-piperazinyl]-phenyl]-2,4-imidazolidinedione; mp. 287.1° C.; (54)
3-butyl-1-[4-[4-(4-hydroxyphenyl)-1-piperazinyl]-phenyl]-2,4-imidazolidinedione; mp. 212.2° C.; (55)
1-[4-[4-(4-hydroxyphenyl)-1-piperazinyl]phenyl]-3-methyl-2,4-imidazolidinedione (56); and
1-[4-[4-(4-hydroxyphenyl)-1-piperazinyl]phenyl]-3-methyl-2-imidazolidinone (57).

EXAMPLE XIII

Gazeous hydrogen bromide was bubbled through 150 parts of cold a hydrobromic acid solution 48% in water. 18.3 Parts of N-(2,2-dimethoxyethyl)-N'-[4-[4-(4-methoxyphenyl)-1-piperazinyl]phenyl]-N-(1-methylethyl)thiourea were added and the whole was stirred first for 1 hours at room temperature and for 2 hours at reflux. After cooling overnight, the precipitated product was filtered off, washed with 2-propanol and dissolved in a mixture of methanol and water. The solution was neutralized with a sodium hydrogen carbonate solution. The product was extracted with dichloromethane. The extract was dried, filtered and evaporated. The residue was boiled in methanol. After cooling, the product was filtered off and purified by column chromatography over silica gel using a mixture of trichloromethane and methanol (98:2 by volume) as eluent. The pure fractions were collected and the eluent was evaporated. The residue was crystallized from 1-butanol. The product was filtered off and dried, yielding 10.5 parts (68%) of 4-[4-[4-[[3-(1-methylethyl)-2(3H)-thiazolyliden]amino]phenyl]-1-piperazinyl]-phenol; mp. 215.7° C. (58).

EXAMPLE XIV

Gazeous hydrogen bromide was bubbled through a stirred mixture of 150 parts of a hydrobromic acid solution 48% in water and 1 part of sodium sulfite. 16.5 Parts of N-(2,2-dimethoxyethyl)-N'-[4-[4-(4-methoxyphenyl)-1-piperazinyl]phenyl]-N-methylthiourea were added and the whole was stirred and refluxed for 3 hours. After cooling, the precipitated product was filtered off, washed with 2-propanol and dissolved in a mixture of methanol and water. The solution was treated with sodium hydrogen carbonate. The product was extracted with dichloromethane. The precipitated product was filtered off and purified by column chromatography over silica gel using a mixture of trichloromethane and methanol (98:2 by volume) as eluent. The pure fractions were collected and the eluent was evaporated. The residue was triturated in dichloromethane. The product was filtered off and dried, yielding 6 parts (44%) of 4-[4-[4-[(3-methyl-2(3H)-thiazolyliden)amino]phenyl]-1-piperazinyl]phenol; mp. 225° C. (59).

In a similar manner there were also prepared:
4-[4-[4-[(3-ethyl-2(3H)-thiazolyliden)amino]phenyl]-1-piperazinyl]phenol; mp. 198.6° C. (60); and
4-[4-[4-[[3-(1-methylpropyl)-2(3H)-thiazolyliden)amino]phenyl]-1-piperazinyl]phenol; mp. 160° C. (61).

EXAMPLE XV

A mixture of 456 parts of 1-[[2-(2-bromo-4-chlorophenyl)-1,3-dioxolan-2-yl]methyl]-1H-1,2,4-triazole and 1584 parts of concentrate hydrochloric acid was stirred and refluxed for 4 hours. The whole was treated with a sodium hydroxide solution 50%. After stirring for a while, the precipitated product I was filtered off, washed with water and set aside. The filtrate was extracted first twice with 4-methyl-2-pentanone and then three times with trichloromethane. The 4-methyl-2-pentanone layers were dried, filtered and evaporated. The residue was stirred in 2-propanol. The precipitated product II was filtered off and set aside. The trichloromethane-layers were dried, filtered and evaporated. The residue was stirred in 2-propanol. The precipitated product was filtered off and purified, together with product I and product II which were set aside, by column chromatography over silica gel using a mixture of dichloromethane, ethanol and ammonium hydroxide (98.5:1:0.5 by volume) as eluent. The pure fractions were collected and the eluent was evaporated. The residue was crystallized from 2,2'-oxybispropane and 2-propanol. The product was filtered off and dried, yielding 17 parts parts of 1-(2-bromo-4-chlorophenyl)-2-(1H-1,2,4-triazol-1-yl)ethanone (62).

EXAMPLE XVI

A mixture of 30 parts of 1,2,3-propanetriol, 25 parts of 1-(2-bromo-4-chlorophenyl)-2-(1H-1,2,4-triazol-1-yl)ethanone, 296 parts of methanesulfonic acid and 180 parts of benzene was stirred and refluxed for 5 hours. The whole was stirred overnight at room temperature. The reaction mixture was added dropwise to a sodium hydrogen carbonate solution. The product was extracted with trichloromethane. The extract was washed with water, dried, filtered and evaporated. The residue was purified by column chromatography (HPLC) over silica gel using a mixture of trichloromethane, hexane and methanol (46:46:8 by volume) as eluent. The pure fractions were collected and the eluent was evaporated, yielding 13 parts (43%) of cis-2-(2-bromo-4-chlorophenyl)-2-(1H-1,2,4-triazol-1-ylmethyl)-1,3-dioxolane-4-methanol; mp. 150° C. (63).

In a similar manner there were also prepared:
(cis+trans)-2-(4-bromophenyl)-2-(1H-1,2,4-triazol-1-ylmethyl)-1,3-dioxolane-4-methanol as residue (64);
cis-2-(4-chlorophenyl)-2-(1H-1,2,4-triazol-1-ylmethyl-1,3-dioxolane-4-methanol as a residue (65).

EXAMPLE XVII

To a stirred mixture of 37 parts of (cis+trans)-2-(2-chlorophenyl)-2-(1H-1,2,4-triazol-1-ylmethyl-1,3-dioxolane-4-methanol, 500 parts of pyridine and 650 parts of dichloromethane were added dropwise 37 parts of benzoyl chloride at a temperature below 20° C. Upon completion, stirring was continued for 3 hours at room temperature. The reaction mixture was poured onto water and the solution was treated with sodium hydrogen carbonate. The product was extracted with trichloromethane. The extract was washed with water, dried, filtered and evaporated. The residue was purified twice by column chromatography (HPLC) over silica gel using first a mixture of hexane, trichloromethane and methanol (60:38:2 by volume) and then a mixture of trichloromethane and methanol (98:5:1.5 by volume) as eluent. The pure fraction (cis-isomer) was collected and the eluent was evaporated, yielding 19 parts (38%) of cis-2-(2-chlorophenyl)-2-(1H-1,2,4-triazol-1-ylmethyl)-1,3-dioxolane-4-methanol benzoate(ester) as a residue (66).

In a similar manner there was also prepared:
cis-2-(4-bromophenyl)-2-(1H-1,2,4-triazol-1-ylmethyl)-1,3-dioxolane-4-methanol benzoate(ester) (67).

EXAMPLE XVIII

A mixture of 17 parts of cis-2-(2-chlorophenyl)-2-(1H-1,2,4-triazol-1-ylmethyl)-1,3-dioxolane-4-methanol benzoate(ester), 35 parts of a sodium hydroxide solution 50%, 150 parts of water and 300 parts of 1,4-dioxane was stirred and refluxed for 30 minutes. After cooling, the reaction mixture was poured onto water. The product was extracted with methylbenzene. The extract was washed with water, dried, filtered and evaporated. The residue was triturated in 2,2'-oxybispropane. The product was filtered off and dried, yielding 11 parts (88%) of cis-2-(2-chlorophenyl)-2-(1H-1,2,4-triazol-1-ylmethyl)-1,3-dioxolane-4-methanol; mp. 87.2° C. (68).

In a similar manner there was also prepared:
cis-2-(4-bromophenyl)-2-(1H-1,2,4-triazol-1-ylmethyl)-1,3-dioxolane-4-methanol ethanedioate(1:1); mp. 165.5° C. (69).

EXAMPLE XIX

To a stirred mixture of 11 parts of cis-2-(2-chlorophenyl)-2-(1H-1,2,4-triazol-1-ylmethyl)-1,3-dioxolane-4-methanol, 150 parts of pyridine and 195 parts of dichloromethane were added 6 parts of methanesulfonyl chloride. Stirring was continued for 3 hours at room temperature. The reaction mixture was poured onto water and the product was extracted with trichloromethane. The extract was washed with water, dried, filtered and evaporated. The residue was triturated in 2,2'-oxybispropane and 4-methyl-2-pentanone. The product was filtered off and dried, yielding 13.6 parts (98%) of cis-2-(2-chlorophenyl)-2-(1H-1,2,4-triazol-1-ylmethyl)-1,3-dioxolane 4-methanol methanesulfonate(ester); mp. 100.0° C. (70).

In a similar manner there were also prepared:
cis-2-(4-chlorophenyl)-2-(1H-1,2,4-triazol-1-ylmethyl-1,3-dioxolane-4-methanol methanesulfonate (ester); (71)
cis-2-(4-bromophenyl)-2-(1H-1,2,4-triazol-1-ylmethyl)-1,3-dioxolane-4-methanol methanesulfonate (ester) ethanedioate(1:1) (72);
cis-2-(2-bromo-4-chlorophenyl)-2-(1H-1,2,4-triazol-1-ylmethyl)-1,3-dioxolane-4-methanol methanesulfonate(ester) (73);
cis-2-(2-chloro-4-fluorophenyl)-2-(1H-imidazol-1-ylmethyl)-1,3-dioxolane-4-methanol methanesulfonate (ester) (74); and
cis-2-(4-fluorophenyl)-2-(1H-imidazol-1-ylmethyl)-1,3-dioxolane-4-methanol methanesulfonate(ester) ethanedioate (1:1) (75).

EXAMPLE XX (a) To 11.9 parts of water was added dropwise 11.5 parts of sulfuric acid with stirring and while cooling. Then there was added portionwise 4.6 parts of dl-1-(4-methoxyphenyl)-2-methyl-4-(4-methylphenylsulfonyl)-piperazine and after addition was complete, the whole was stirred and refluxed for 20 hours. After cooling the reaction mixture was poured onto crushed ice. The whole was alkalized with sodium hydroxide solution 15N and extracted three times with 4-methyl-2-pentanone. The combined extracts were dried over potassium carbonate and evaporated. The oily residue was distilled in vacuo, yielding 1.7 parts of oily 1-(4-methoxyphenyl)-2-methylpiperazine; bp. 144°–147° C. at 0.3 mm pressure; $n_D^{20} = 1.5633$; $d_{20}^{20} = 1.0782$ (76).

(b) A mixture of 43 parts of 1-(4-methoxyphenyl)-2-methylpiperazine and 375 parts of a hydrobromic acid solution 48% in water was stirred and refluxed overnight. The reaction mixture was evaporated and the residue was crystallized from 2-propanol. The product was filtered off and dried, yielding 72 parts (97%) of 4-(2-methyl-1-piperazinyl)phenol dihydrobromide (77).

(c) To a stirred mixture of 69 parts of 4-(2-methyl-1-piperazinyl)phenyl dihydrobromide, 50 parts of sodium hydrogen carbonate, 500 parts of water and 450 parts of trichloromethane were added 21 parts of acetic acid anhydride. Stirring was continued for 1 hour at room temperature. The organic phase was separated, dried, filtered and evaporated. The residue was dissolved in a dilute sodium hydroxide solution and stirred overnight. The whole was neutralized with acetic acid and sodium hydrogen carbonate. The precipitated product was filtered off and triturated in 4-methyl-2-pentanone. The product was filtered off and crystallized from 2-propanol, yielding 22.8 parts of 1-acetyl-4-(4-hydroxyphenyl)-3-methylpiperazine; mp. 175.9° C. (78).

(d) A mixture of 19 parts of 1-acetyl-4-(4-hydroxyphenyl)-3-methylpiperazine, 36 parts of cis-2-(2,4-dichlorophenyl)-2-(1H-1,2,4-triazol-1-ylmethyl)-1,3-dioxolane-4-methanol methanesulfonate(ester), 6.5 parts of potassium hydroxide and 200 parts of dimethyl sulfoxide was stirred overnight at room temperature. The reaction mixture was poured onto water and the product was extracted with dichloromethane. The extract was washed with water, dried, filtered and evaporated. The residue was purified by filtration over silica gel using a mixture of trichloromethane and methanol (98:2 by volume) as eluent. The filtrate was evaporated and the residue was crystallized from a mixture of 4-methyl-2-pentanone and 1,1'-oxybisethane, yielding 23.3 parts (52%) of cis-1-acetyl-4-[4-[[2-(2,4-dichlorophenyl)-2-(1H-1,2,4-triazol-1-ylmethyl)-1,3-dioxolan-4-yl]-methoxy]phenyl]-3-methylpiperazine; mp. 128.6°–131.3° C. (79).

(e) A mixture of 21.3 parts of cis-1-acetyl-4-[4-[[2-(2,4-dichlorophenyl)-2-(1H-1,2,4-triazol-1-ylmethyl)-1,3-dioxolan-4-yl]methoxy]phenyl]-3-methylpiper azine and 200 parts of a hydrochloric acid solution 1N was stirred for 5 hours at 80° C. The reaction mixture was cooled and neutralized with sodium hydrogen carbonate. The product was extracted with dichloromethane. The extract was dried, filtered and evaporated. The residue was crystallized from 1,1'-oxybisethane, yielding 11.7 parts (59%) of cis-1-[4-[[2-(2,4-dichlorophenyl)-2-(1H-1,2,4-triazol-1-ylmethyl)-1,3-dioxolan-4-yl]methoxy]phenyl]-2-methylpiperazine; mp. 125° C. (80).

(f) A mixture of 4.2 parts of 1-fluoro-4-nitrobenzene, 14 parts of cis-1-[4-[[2-(2,4-dichlorophenyl)-2-(1H-1,2,4-triazol-1-ylmethyl)-1,3-dioxolan-4-yl]methoxy]phenyl]-2-methylpiperazine, 2 parts of potassium carbonate and 150 parts of dimethyl sulfoxide was stirred for 1 hour at 100° C. The reaction mixture was cooled and poured onto water. The product was extracted with dichloromethane. The extract was washed with water, dried, filtered and evaporated. The residue was crystallized from a small amount of 4-methyl-2-pentanone and 1,1'-oxybisethane, yielding 14 parts (80%) of cis-1-[4-[[2-(2,4-dichlorophenyl)-2-(1H-1,2,4-triazol-1-ylmethyl)-1,3-dioxolan-4-yl]methoxy]phenyl]-2-methyl-4-(4-nitrophenyl)piperazine; mp. 133.7° C. (81).

(g) A mixture of 12 parts of cis-1-[4-[[2-(2,4-dichlorophenyl)-2-(1H-1,2,4-triazol-1-ylmethyl)-1,3-dioxolan-4-yl]methoxy]phenyl]-2-methyl-4-(4-nitr ophenyl)piperazine, 1 part of a solution of thiophene in ethanol 4% and 300 parts of 2-methoxyethanol was hydrogenated at normal pressure and at 50° C. with 2 parts of platinum-on-charcoal catalyst 5%. After the calculated amount of hydrogen was taken up, the catalyst was filtered off and the filtrate was evaporated, yielding 11.4 parts (100%) of cis-4-[4-[4-[[2-(2,4-dichlorophenyl)-2-(1H-1,2,4-triazol-1-ylmethyl)-1,3-dioxolan-4-yl]methoxy]-phenyl]-3-methyl-1-piperaz inyl]benzenamine as a residue (82).

EXAMPLE XXI

A mixture of 4.1 parts of 1-butyl-3-[4-[4-(4-hydroxyphenyl)-1-piperazinyl]phenyl]-2,4-imidazolidinedione, 6.2 parts of cis-2-(4-chlorophenyl)-2-(1H-1,2,4-triazol-1-ylmethyl-1,3-dioxolane-4-methanol methanesulfonate (ester) ethanedioate(1:1), 10.0 parts of potassium carbonate and 180 parts of 1-propanol was stirred and refluxed for 1 week. After cooling, the reaction mixture was diluted with water. The product was extracted three times with dichloromethane. The combined extracts were dried, filtered and evaporated in vacuo. The residue was triturated in acetonitrile. The precipitated product was filtered off and purified by column chromatography over silica gel using a mixture of trichloromethane and methanol (99:1 by volume) as eluent. The pure fractions were collected and the eluent was evaporated. The residue was crystallized from 4-methyl-2-pentanone, yielding 2.5 parts (39%) of propyl cis-[4-[4-[4-[[2-(4-chlorophenyl)-2-(1H-1,2,4-triazol-1-ylmethyl)-

1,3-dioxolan-4-yl]methoxy]phenyl]-1-piperazinyl]-phenyl]carbamate; mp. 210.7° C. (83).

In a similar manner there was also prepared:

Following the same procedure and using equivalent amounts of the appropriate starting materials there were also prepared:

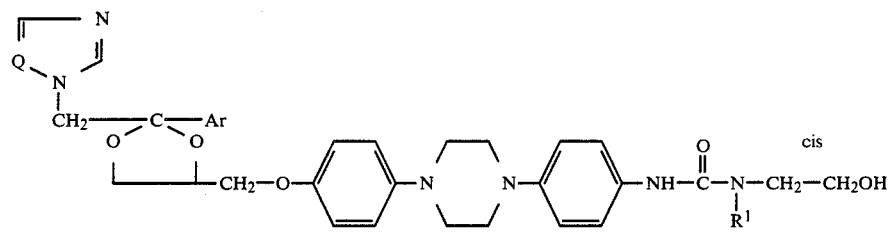

| Int. No. | Q | Ar | R¹ | mp. in °C. |
|---|---|---|---|---|
| (86) | CH | 2,4-dichlorophenyl | $C_2H_5$ | 137.4 |
| (87) | N | 2,4-dichlorophenyl | $C_2H_5$ | 159.8 |
| (88) | N | 2,4-dichlorophenyl | $n.C_3H_7$ | 157.8 |
| (89) | N | 2,4-dichlorophenyl | $n.C_4H_9$ | 151.9 |
| (90) | N | 2,4-dichlorophenyl | $(CH_3)_2CH$ | 176.8 |
| (91) | N | 2,4-dichlorophenyl | $C_2H_5(CH_3)CH$ | 176.5 |
| (92) | N | 2,4-dichlorophenyl | $i.C_4H_9$ | 136.5 |
| (93) | N | 2,4-dichlorophenyl | $(CH_3)_2CHCH_2CH_2$ | 162.7 |
| (94) | N | 2,4-dichlorophenyl | $C_2H_5(CH_3)CHCH_2$ | 136.8 |
| (95) | N | 2,4-dichlorophenyl | $(C_2H_5)_2CH$ | 174.3 |
| (96) | N | 2,4-dichlorophenyl | $n.C_3H_7(CH_3)CH$ | 139.4 |
| (97) | CH | 2,4-dichlorophenyl | $C_2H_5(CH_3)CH$ | 190.0 |
| (98) | N | 2,4-dichlorophenyl | $n.C_5H_{11}$ | 159.5 |
| (99) | CH | 2,4-dichlorophenyl | H | 201.2 |
| (100) | CH | 2,4-dichlorophenyl | $n.C_4H_9$ | 168.6 |
| (101) | CH | 2,4-dichlorophenyl | $n.C_3H_7$ | 166.2 |
| (102) | CH | 2,4-dichlorophenyl | $CH_3$ | 170.2 |
| (103) | N | 2,4-dichlorophenyl | $C_2H_5$ | 106.1–120.2 | propyl cis-[4-[4-[4-[[2-(4-bromophenyl)-2-(1H-1,2,4-triazol-1-ylmethyl)-1,3-dioxolan-4-yl]methoxy]-phenyl]-1-piperazinyl]phenyl]carbamate; mp. 214.4° C. (84).

EXAMPLE XXII

A mixture of 2 parts of 2-(methylamino)ethanol, 10 parts of cis-phenyl [4-[4-[4-[2-(2,4-dichlorophenyl)-2-(1H-1,2,4-triazol-1-ylmethyl)-1,3-dioxolan-4-ylmethoxy]phenyl]-1-piperazinyl]phenyl]carbamate and 150 parts of 1,4-dioxane was stirred and refluxed for 4 hours. To the reaction mixture were added 35 parts of 2,2'-oxybispropane. The product was allowed to crystallize. It was filtered off and triturated in 2-propanone. The product was filtered off and dried, yielding 9 parts (92%) of cis-N-4-[4-[4-[[2-(2,4-dichlorophenyl)-2-(1H-1,2,4-triazol-1-ylmethyl)-1,3-dioxolan-4-yl]methoxy]-pheny l]-1-piperazinyl]phenyl]-N'-(2-hydroxyethyl)-N'-methylurea; mp. 185.4° C. (85).

In a similar manner there were also prepared:

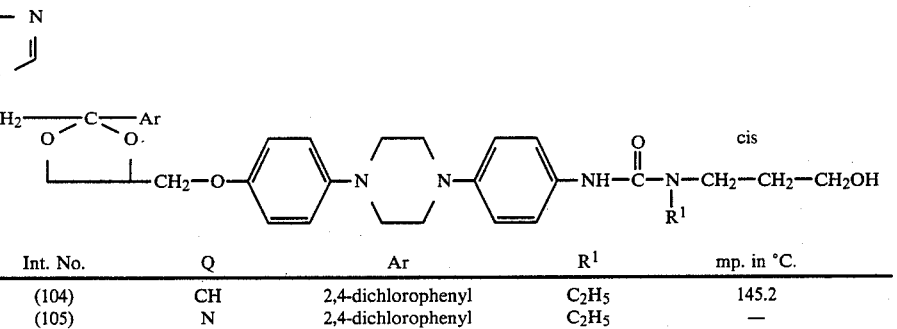

| Int. No. | Q | Ar | R¹ | mp. in °C. |
|---|---|---|---|---|
| (104) | CH | 2,4-dichlorophenyl | $C_2H_5$ | 145.2 |
| (105) | N | 2,4-dichlorophenyl | $C_2H_5$ | — |

EXAMPLE XXIII

A mixture of 5 parts of 2,2-dimethoxyethanamine, 22 parts of cis-phenyl [4-[4-[4-[2-(2,4-dichlorophenyl)-2-(1H-1,2,4-triazol-1-ylmethyl)-1,3-dioxolan-4-ylmethoxy]phenyl]-1-piperazinyl]phenyl]carbamate and 250 parts of 1,4-dioxane was stirred and refluxed overnight. The reaction mixture was cooled to about 50° C. and treated with activated charcoal. The latter was filtered off and the filtrate was saturated with 2,2'-oxybispropane. The precipitated product was filtered off and crystallized from 2-propanol, yielding 16 parts (71%) of cis-phenyl [4-[4-[4-[2-(2,4-dichlorophenyl)-2-(1H-1,2,4-triazol-1-ylmethyl)-1,3-dioxolan-4-ylmethoxy]phenyl]-1-piperazinyl]phenyl]-N'-(2,2-dimethoxyethyl)urea; mp. 151.7° C. (106).

In a similar manner there was also prepared:
cis-N-[4-[4-[4-[2-(2,4-dichlorophenyl)-2-(1H-imidazol-1-ylmethyl)-1,3-dioxolan-4-ylmethoxy]phenyl]-1- piperazinyl]phenyl]-N'-(2,2-dimethoxyethyl)urea (107).

EXAMPLE XXIV

A mixture of 2.2 parts of 2-(phenylamino)ethanol, 10 parts of phenyl cis-[4-[4-[4-[2-(2,4-dichlorophenyl)-2-(1H-1,2,4-triazol-1-ylmethyl)-1,3-dioxolan-4-ylmethoxy]phenyl]-1-piperazinyl]phenyl]carbamate, 2 parts of N,N-dimethyl-4-pyridinamine and 200 parts of 1,4-dioxane was stirred and refluxed overnight. The reaction mixture was cooled and poured onto water. The product was extracted with dichloromethane. The extract was washed with water, dried, filtered and evaporated. The residue was purified by column chromatography over silica gel using a mixture of trichloromethane and methanol (99:1 by volume) as eluent. The pure fractions were collected and the eluent was evaporated. The residue was crystallized twice from 4-methyl-2-pentanone (activated charcoal), yielding 3.8 parts (36%) of 2-(phenylamino)ethyl cis-[4-[4-[4-[2-(2,4-dichlorophenyl)-2-(1H-1,2,4-triazol-1-ylmethyl)-1,3-dioxolan-4-ylmethoxy]phenyl]-1-piperazinyl]phenyl]carbamate; mp. 188.1° C. (108).

EXAMPLE XXV

A mixture of 1.8 parts of 2-(ethylamino)ethanol, 10 parts of cis-1-[4-[[2-(2,4-dichlorophenyl)-2-(1H-imidazol-1-ylmethyl)-1,3-dioxolan-4-yl]methoxy]phenyl]-4-(4-isothiocyanatophenyl)piperazine and 160 parts of ethanol was stirred till all solid entered solution. Upon stirring, the reaction mixture was allowed to cool. The crystallized product was filtered off and dried, yielding 9 parts (79%) of cis-N-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-N'-ethyl-N'-(2-hydroxyethyl)thiourea; mp. 171.5° C. (109).

In a similar manner there was also prepared:
cis-N-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-N'-(2-hydroxyethyl)-N'-(1-methylpropyl)thiourea; mp. 173.4° C. (110).

EXAMPLE XXVI

A mixture of 5 parts of 2-[(3-methylbutyl)amino]ethanol, 20 parts of cis-1-[4-[[2-(2,4-dichlorophenyl)-2-(1H-imidazol-1-ylmethyl)-1,3-dioxolan-4-yl]methoxy]phenyl]-4-(4-isothiocyanatophenyl)piperazine and 390 parts of dichloromethane was stirred for 1 hour at room temperature. The reaction mixture was evaporated and the residue was crystallized from 4-methyl-2-pentanone. The product was filtered off and dried, yielding 19.7 parts (81%) of cis-N'-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-N-(2-hydroxyethyl)-N-(3-methylbutyl)thiourea; mp. 166.0° C. (111).

Following the same procedure and using equivalent amounts of the appropriate starting materials there were also prepared:

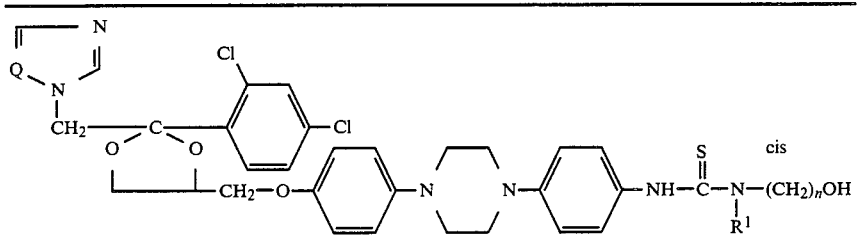

| Int. No. | Q | n | R$^1$ | mp. in °C. |
|---|---|---|---|---|
| (112) | CH | 2 | (CH$_3$)$_2$CH | 137.7 |
| (113) | CH | 2 | n.C$_3$H$_7$ | 155.1 |
| (114) | CH | 2 | i.C$_4$H$_9$ | 170.0 |
| (115) | N | 2 | C$_2$H$_5$ | 179.6 |
| (116) | N | 2 | C$_2$H$_5$(CH$_3$)CH | 169.3 |
| (117) | CH | 2 | n.C$_4$H$_9$ | 180.4 |
| (118) | N | 2 | n.C$_3$H$_7$ | 178.5–178.9 |
| (119) | N | 2 | (CH$_3$)$_2$CH | 190.0 |
| (120) | CH | 2 | CH$_3$ | 153.5 |
| (121) | N | 2 | n.C$_5$H$_{11}$ | 154.7 |
| (122) | N | 2 | (CH$_3$)$_2$CHCH$_2$ | 180.0 |
| (123) | CH | 2 | n.C$_5$H$_{11}$ | 153.1 |
| (124) | N | 2 | CH$_3$ | 175.2 |
| (125) | CH | 2 | (C$_2$H$_5$)$_2$CH | 181.4 |
| (126) | CH | 2 | C$_2$H$_5$(CH$_3$)CHCH$_2$ | 165.0 |
| (127) | N | 2 | (C$_2$H$_5$)$_2$CH | 162.8 |
| (128) | N | 2 | n.C$_4$H$_9$ | 144.9 |
| (129) | N | 2 | n.C$_3$H$_7$(CH$_3$)CH | 116.7 |
| (130) | N | 2 | C$_2$H$_5$(CH$_3$)CHCH$_2$ | 120.0 |
| (131) | N | 2 | i.C$_5$H$_{11}$ | — |
| (132) | N | 3 | C$_2$H$_5$ | 166.6 |
| (133) | CH | 3 | C$_2$H$_5$ | 165.0 |
| (134) | N | 3 | n.C$_4$H$_9$ | 147.5 |
| (135) | CH | 3 | n.C$_4$H$_9$ | 172.9 |
| (136) | CH | 3 | i.C$_3$H$_7$ | 156.4 |

EXAMPLE XXVII

A mixture of 4 parts of 2-(phenylamino)ethanol, 10 parts of cis-1-[4-[[2-(2,4-dichlorophenyl)-2-(1H-imidazol-1-ylmethyl)-1,3-dioxolan-4-yl]methoxy]phenyl]-4-(4-isothiocyanatophenyl)piperazine, 1 part of N,N-dimethyl-4-pyridinamine and 39 parts of dichloromethane was stirred overnight at room temperature. The reaction mixture was evaporated. The residue was crystallized from 2-propanone. The product was filtered off and dried, yielding 10.5 parts (86%) of cis-N-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-N'-(2-hydroxyethyl)-N'-phenylthiourea; mp. 131.7° C. (137).

EXAMPLE XXVIII

A mixture of 10 parts of 2-(phenylamino)ethanol and 10 parts of cis-1-[4-[[2-(2,4-dichlorophenyl)-2-(1H-1,2,4-triazol-1-ylmethyl)-1,3-dioxolan-4-yl]methoxy]phenyl]-4-(4-isothiocyanatophenyl)piperazine was stirred and heated till all entered solution. The whole was stirred overnight at 50° C. The residue was taken up in a mixture of trichloromethane and methanol (90:10 by volume). The solution was washed twice with a dilute hydrochloric acid solution and once with a sodium hydrogen carbonate solution. The mixture was evaporated. The residue was purified by column chromatography over silica gel using a mixture of trichloromethane and methanol (99:1 by volume) as eluent. The pure fractions were collected and the eluent was evaporated, yielding 10 parts (82%) of cis-N'-[4-[4-[4-[[2-(2,4-dichlorophenyl)-2-(1H-1,2,4-triazol-1-yl-methyl)-1,3-dioxolan-4-yl]methoxy]phenyl]-1-pipera zinyl]phenyl]-N-(2-hydroxyethyl)-N-phenylthiourea as a residue (138).

EXAMPLE XXIX

A solution of 17 parts of 1H-imidazole-2-methanamine dihydrochloride, 10.7 parts of benzaldehyde, 2 parts of a solution of thiophene in methanol 4%, 20 parts of potassium acetate and 200 parts of methanol was hydrogenated at normal pressure and at 50° C. with 2 parts of platinum-on-charcoal catalyst 5%. After the calculated amount of hydrogen was taken up, the catalyst was filtered off and the filtrate was evaporated. The residue was dissolved in water and the solution was treated with ammonium hydroxide. The product was extracted with dichloromethane. The extract was dried, filtered and evaporated, yielding 15 parts (80%) of N-(phenylmethyl)-1H-imidazole-2-methanamine as a residue (139).

In a similar manner there was also prepared:
cis-N'-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N-ethyl-N-[2-(ethylamino)ethyl]thiourea; mp. 149.6° C. (140).

EXAMPLE XXX

A mixture of 2.1 parts of 2,2-dimethoxy-N-methylethanamine, 10 parts of cis-1-[4-[[2-(2,4-dichlorophenyl)-2-(1H-imidazol-1-ylmethyl)-1,3-dioxolan-4-yl]methoxy]phenyl]-4-(4-isothiocyanatophenyl)piperazine and 130 parts of dichloromethane was stirred for 2 hours at room temperature. The reaction mixture was evaporated and the residue was crystallized from methanol. The product was filtered off and dried, yielding 11.6 parts (97.8%) of cis-N'-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-N-(2,2-dimethoxyethyl)-N-methylthiourea; mp. 164.6° C. (141).

In a similar manner there were also prepared:
cis-N'-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N-(2,2-dimet hoxyethyl)-N-phenylmethylthiourea; mp. 129.7° C. (142);

cis-N'-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-N-(2,2-dimethoxyethyl)-N-ethylthiourea; mp. 115.4° C. (143);

cis-N'-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-N-(2,2-dimethoxy)-N-(1-methylpropyl)thiourea; mp. 141.0° C. (144);

cis-N'-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N-(2,2-dimet hoxyethyl)-N-methylthiourea; mp. 139.2° C. (145);

cis-N'-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N-(2,2-dimet hoxyethyl)-N-ethylthiourea; mp. 139.5° C. (146);

cis-N'-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-N-(2,2-dimethoxyethyl)-N-(1-methylethyl)thiourea; mp. 143.9° C. (147);

cis-N'-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N-(2,2-dimet hoxyethyl)-N-(1-methylpropyl)thiourea as a residue (148); and cis-N'-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N-(2,2-dimet hoxyethyl)-N-(1-methylethyl)thiourea monohydrate; mp. 128.1° C. (149).

EXAMPLE XXXI

To a stirred mixture of 0.91 parts of methylhydrazine in 195 parts of cis-N-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-1-methylhydrazinecarbothioamide were added 10 parts of cis-1-[4-[[2-(2,4-dichlorophenyl)-2-(1H-1,2,4-triazol-1-ylmethyl)-1,3-dioxolan-4-yl]methoxy]phenyl]-4-(4-isothiocyanatophenyl)piperaz ine. The whole was stirred for 1 hour. The reaction mixture was evaporated. The residue was triturated in methanol. The product was filtered off and crystallized from 1-butanol. The product was filtered off and dried, yielding 7.2 parts (67%) of cis-N-[4-[4-[4-[[2-(2,4-dichlorophenyl)-2-(1H-1,2,4-triazol-1-ylmethyl)-1,3-dioxolan-4-yl]methoxy]phenyl]-1-piperaziny l]phenyl]-1-methylhydrazinecarbothioamide; mp. 171.3° C. (150).

EXAMPLE XXXII

A mixture of 5.2 parts of N,N-dimethyl-N'-(1-methylpropyl)methanehydrazonamide, 12.5 parts of cis-1-[4-[[2-(2,4-dichlorophenyl)-2-(1H-1,2,4-triazol-1-ylmethyl)-1,3-dioxolan-4-yl]methoxy]phenyl]-4-(4-isothiocyanatophenyl)piperazine and 300 parts of trichloromethane was stirred for 5 hours at room temperature. The reaction mixture was evaporated. The residue was purified by column chromatography over silica gel using a mixture of trichloromethane and methanol (resp. 99:1 and 97.5:2.5 by volume) as eluent. The pure fractions were collected and the eluent was evaporated. The residue was crystallized from methanol, yielding 7.2 parts (53%) of cis-N'-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N,N-dimethylthiourea; mp. 185.0° C. (151).

EXAMPLE XXXIII

To a stirred solution of 5 parts of cis-4-[4-[4-[2-(2,4-dichlorophenyl)-2-(1H-imidazol-1-ylmethyl)-1,3-dioxolan-4-ylmethoxy]phenyl]-1-piperazinyl]benzenamine in 50 parts of pyridine were added dropwise 0.85 parts of methyl carbonochloridate. Upon completion, stirring was continued for 1 hour. Another 0.85 parts of methyl carbonochloridate was added dropwise and stirring was continued for 2 hours at room temperature. The reaction mixture was poured onto water. The precipitated product was filtered off and dried. It was purified by column chromatography over silica gel using a mixture of trichloromethane and methanol (98:2 by volume) as eluent. The pure fractions were collected and the eluent was evaporated. The residue was crystallized from 1-butanol, yielding 4.5 parts (82%) of cis-methyl [4-[4-[4-[2-(2,4-dichlorophenyl)-2-(1H-imidazol-1-ylmethyl]-1,3-dioxolan-4-ylmethoxy]phenyl]-1-piperazinyl]phenyl]carbamate; mp. 208.6° C. (152).

EXAMPLE XXXIV

To a stirred solution of 5 parts of cis-4-[4-[4-[2-(2,4-dichlorophenyl)-2-(1H-imidazol-1-ylmethyl)-1,3-dioxolan-4-ylmethoxy]phenyl]-1-piperazinyl]benzenamine in 130 parts of dichloromethane were added successively 0.8 parts of ethyl chloroformate and 1 part of sodium hydrogen carbonate in 50 parts of water. The whole was stirred for one hour at room temperature. 140 Parts of petroleumether were added to the reaction mixture. The precipitated product was filtered off, washed with water and 2-propanol, and purified by column chromatography over silica gel using a mixture of trichloromethane and methanol (97:3 by volume) as eluent. The pure fractions were collected and the eluent was evaporated. The residue was crystallized from a mixture of 1,4-dioxane and 2,2'-oxybispropane, yielding 4.6 parts of cis-ethyl [4-[4-[4-[2-(2,4-dichlorophenyl)-2-(1H-imidazol-1-ylmethyl]-1,3-dioxolan-4-ylmethoxy]phenyl]-1-piperazinyl]phenyl]carbamate; mp. 206.7° C. (153).

In a similar manner there were also prepared:

cis-ethyl [4-[4-[4-[2-(2,4-dichlorophenyl)-2-(1H-1,2,4-triazol-1-ylmethyl]-1,3-dioxolan-4-ylmethoxy]phenyl]-1-piperazinyl]phenyl]carbamate; mp. 202° C. (154); and cis-methyl [4-[4-[4-[2-(2,4-dichlorophenyl)-2-(1H-1,2,4-triazol-1-ylmethyl]-1,3-dioxolan-4-ylmethoxy]phenyl]-1-piperazinyl]phenyl]carbamate; mp. 205.5° C. (155).

EXAMPLE XXXV

A mixture of 0.73 parts of isothiocyanatomethane, 5 parts of cis-4-[4-[4-[2-(2,4-dichlorophenyl)-2-(1H-imidazol-1-ylmethyl)-1,3-dioxolan-4-ylmethoxy]phenyl]-1-piperazinyl]benzenamine, 130 parts of dichloromethane and 100 parts of 1,4-dioxane was stirred and refluxed for 4 hours. Another 0.73 parts of isothiocyanatomethane were added and stirring at reflux temperature was continued overnight. The reaction mixture was evaporated and the residue was crystallized from 2-propanol. The product was filtered off and recrystallized from 1-butanol (activated charcoal), yielding 3.2 parts (57%) of cis-N-[4-[4-[4-[2-(2,4-dichlorophenyl)-2-(1H-imidazol-1-ylmethyl)-1,3-dioxolan-4-ylmethoxy]phenyl 9 -1-piperazinyl]phenyl]-N'-methylthiourea; mp. 172.5° C. (156).

EXAMPLE XXXVI

A mixture of 0.9 parts of 1-isocyanatopropane, 5.8 parts of cis-4-[4-[4-[2-(2,4-dichlorophenyl)-2-(1H-imidazol-1-ylmethyl)-1,3-dioxolan-4-ylmethoxy]phenyl]-1-piperazinyl]benzenamine and 260 parts of dichloromethane was stirred overnight at room temperature. The reaction mixture was evaporated. The residue was purified by column chromatography over silica gel using a mixture of trichloromethane and methanol (99:1 by volume) as eluent. The pure fractions were collected and the eluent was evaporated. The residue was crystallized from 4-methyl-2-pentanone (activated charcoal), yielding 3.4 parts (51%) of cis-N-[4-[4-[4-[2-(2,4-dichlorophenyl)-2-(1H-imidazol-1-ylmethyl)-1,3-dioxolan-4-ylmethoxy]phenyl]-1-piperazinyl]phenyl]-N'-propyl urea; mp. 228.6° C. (157).

In a similar manner there were also prepared:

cis-N-[4-[4-[4-[2-(2,4-dichlorophenyl)-2-(1H-imidazol-1-ylmethyl)-1,3-dioxolan-4-ylmethoxy]phenyl]-1-piperazinyl]phenyl]-N'-methylurea; mp. 192.6° C.; (158)

cis-N-[4-[4-[4-[2-(2,4-dichlorophenyl)-2-(1H-1,2,4-triazol-1-yl methyl)-1,3-dioxolan-4-ylmethoxy]phenyl]-1-piperazinyl]phenyl]-N'-methylurea; mp. 203.4° C.; (159)

cis-N-[4-[4-[4-[2-(2,4-dichlorophenyl)-2-(1H-1,2,4-triazol-1-yl methyl)-1,3-dioxolan-4-ylmethoxy]phenyl]-1-piperazinyl]phenyl]-N'-ethylurea; mp. 164.4° C.; (160)

cis-N-[4-[4-[4-[2-(2,4-dichlorophenyl)-2-(1H-imidazol-1-ylmethyl)-1,3-dioxolan-4-ylmethoxy]phenyl]-1-piperazinyl]phenyl]-N'-ethylurea; mp. 217.2° C. (161); and cis-N-[4-[4-[4-[2-(2,4-dichlorophenyl)-2-(1H-1,2,4-triazol-1-yl methyl)-1,3-dioxolan-4-ylmethoxy]phenyl]-1-piperazinyl]phenyl]-N'-propylurea; mp. 194° C. (162).

Following the same procedure and using equivalent amounts of the appropriate starting materials, there were also prepared:

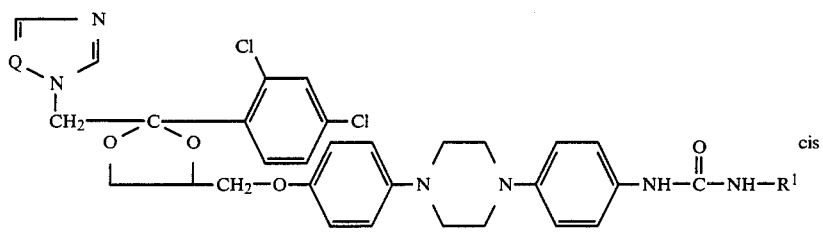

| Int. No. | Q | R¹ | mp. in °C. |
|---|---|---|---|
| (163) | CH | 4-NO$_2$—C$_6$H$_4$ | 219.2 |
| (164) | CH | 2-Cl—C$_6$H$_4$ | 203.4 |
| (165) | N | (C$_2$H$_5$)$_2$CH | 163.8 |
| (166) | CH | (C$_2$H$_5$)$_2$CH | 201.9 |
| (167) | CH | CH$_3$(C$_2$H$_5$)CH | — |
| (168) | CH | CH$_3$(C$_3$H$_7$)CH | 191.4 |
| (169) | CH | 4-CH$_3$—C$_6$H$_4$ | 234.4 |
| (170) | CH | C$_6$H$_5$ | 224.0 |
| (171) | CH | (CH$_3$)$_2$CH(CH$_2$)$_2$ | 209.4 |
| (172) | CH | CH$_3$(CH$_2$)$_4$ | 203.6 |
| (173) | CH | t.C$_4$H$_9$ | 216.9 |
| (174) | N | CH$_3$(C$_2$H$_5$)CH | 161.6 |
| (175) | N | (CH$_3$)$_2$CH(CH$_2$)$_2$ | 196.6 |
| (176) | N | t.C$_4$H$_9$ | 208.1 |
| (177) | N | (CH$_3$)$_2$CHCH$_2$ | 201.8 |
| (178) | N | CH$_3$(CH$_2$)$_4$ | 171.1 |
| (179) | CH | (CH$_3$)$_2$CHCH$_2$ | 221.5 |
| (180) | N | n.C$_4$H$_9$ | 196.0 |
| (181) | N | i.C$_3$H$_7$ | 198.9 |
| (182) | CH | i.C$_3$H$_7$ | 248.9 |
| (183) | CH | n.C$_4$H$_9$ | 196.9 and |
| (184) | CH | 3-Cl—C$_6$H$_4$ | 186.9 |

EXAMPLE XXXVII

A mixture of 4 parts of cis-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-5,5-dimethyl-2,4-imidazolidinedione, 4 parts of potassium hydroxide and 80 parts of ethanol was stirred and refluxed till all solid entered solution. After cooling, the product was filtered off and dissolved in a mixture of methanol and water. The acid was liberated with acetic acid. The product was filtered off, washed with water and methanol and dried, yielding 3 parts (73%) of cis-2-[[[4-[4-[4-[[2-(2,4-dichlorophenyl)-2-(1H-imidazol-1-ylmethyl)-1,3-dioxolan-4-yl]methoxy]phenyl]-1-piperazinyl]-phenyl]aminocarbonyl]-amino]- 2-methylpropanoic acid; mp. 199.3° C. (185).

EXAMPLE XXXVIII

A mixture of 1.92 parts of thionyl chloride, 5 parts of cis-N-[4-[4-[4-[2-(2,4-dichlorophenyl)-2-(1H-imidazol-1-ylmethyl)-1,3-dioxolan-4-ylmethoxy]phenyl]-1-piperazinyl]phenyl]-N'-(2-hydroxyethyl)urea and 225 parts of trichloromethane was stirred and refluxed for 2 hours. The reaction mixture was evaporated and the residue was stirred in 80 parts of methanol. 2 Parts of potassium hydroxide were added and the whole was stirred till the product was precipitated. It was filtered off and purified by column-chromatography over silica gel using a mixture of trichloromethane and methanol (99:1 by volume) as eluent. The pure fractions were collected and the eluent was evaporated. The residue was crystallized from methanol, yielding 1 part (20%) of cis-N-(2-chloroethyl)-N'-[4-[4-[4-[2-(2,4-dichlorophenyl)-2-(1H-imidazol-1-ylmethyl)-1,3-dioxolan-4-yl]methoxy]phenyl 9 -1-piperazinyl]phenyl]urea; mp. 204.6° C. (186).

B. Preparation of Final Compounds

EXAMPLE IXL

A mixture of 40 parts of phenyl cis-[4-[4-[4-[2-(2,4-dichlorphenyl)-2-(1H-imidazol-1-ylmethyl)-1,3-dioxolan-4-ylmethoxy]phenyl]-1-piperazinyl]phenyl]carbamate, 11.3 parts of ethyl 2-aminopropanoate hydrochloride, 3 parts of N,N-dimethyl-4-pyridinamine, 8 parts of sodium hydrogen carbonate and 300 parts of 1,4-dioxane was stirred and refluxed for 4 hours. The reaction mixture was saturated with water and stirring and heating was continued for 30 minutes. The mixture was allowed to cool. The precipitated product was filtered off, washed with water and with 2-propanol and dried in a dry-pistol at 120° C., yielding 37.4 parts (97%) of cis-3-[4-[4-[4-[[2-(2,4-dichlorophenyl)-2-(1H-imidazol-1-ylmethyl)-1,3-dioxolan-4-yl]methox y]phenyl]-1-piperazinyl]phenyl]-5-methyl-2,4-imidazolidinedione; mp. 260.3° C. (compound 1).

In a similar manner there were also prepared:

cis-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-2,4-imidazolidinedion e; mp. 253.6° C. (compound 2).

cis-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-5,5-dimethyl-2,4-imidazolidinedione; mp. 226.3° C. (compound 3); and cis-3-[4-[4-[4-[[2-(4-chlorophenyl)-2-(1H-1,2,4-triazol-1-ylmethyl)-1,3-dioxolan-4-yl]methoxy]phenyl]-1-piperazinyl]phenyl]-5,5-dimethyl- b 2,4-oxazolidinedione; mp. 223.6° C. (compound 4).

EXAMPLE XL

A mixture of 1.5 parts of ethyl 2-[(1-methylethyl-

Following the same procedure and using equivalent amounts of the appropriate starting materials there were also prepared:

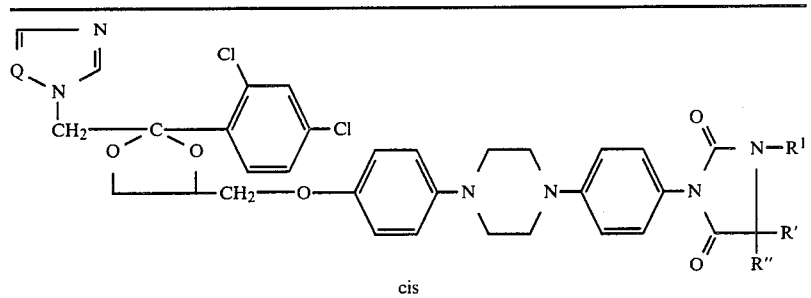

cis

| Compound No. | Q | R¹ | R', R" | mp. in °C. |
|---|---|---|---|---|
| 6 | N | CH₃ | H, H | 197.6 |
| 7 | CH | CH₃ | H, H | 212.7 |
| 8 | N | n.C₄H₉ | H, H | 145.0 |
| 9 | N | n.C₃H₇ | H, H | 150.8 |
| 10 | CH | n.C₃H₇ | H, H | 170.2 |
| 11 | N | C₂H₅ | H, H | 165.1 |
| 12 | CH | n.C₄H₉ | H, H | 135.6 |
| 13 | N | H | CH₃, H | 192.3-202.9 and |
| 14 | N | H | (CH₃)₂ | 178.5-202.5 |

)amino]acetate, 5 parts of cis-phenyl [4-[4-[4-[2-(2,4-dichlorophenyl)-2-(1H-1,2,4-triazol-1-ylmethyl)-1,3-dioxolan-4-ylmethoxy]phenyl]-1-piperazinyl]phenyl]-carbamate, 1 part of N,N-dimethyl-4-pyridinamine and 100 parts of 1,4-dioxane was stirred and refluxed overnight. Water was added followed by the addition of 4-methyl-2-pentanone and 2,2'-oxybispropane. The whole was stirred till the product was crystallized. It is filtered off and recrystallized from 4-methyl-2-pentanone, yielding 4.5 parts (89%) of cis-3-[4-[4-[4-[[2-(2,4-dichlorophenyl)-2-(1H-1,2,4-triazol-1-ylmethyl)-1,3-dioxolan-4-yl]methoxy]phenyl]-1-pipe razinyl]phenyl]-1-(1-methylethyl)-2,4-imidazolidinedione; mp. 178.0° C. (compound 5).

In a similar manner there were also prepared:

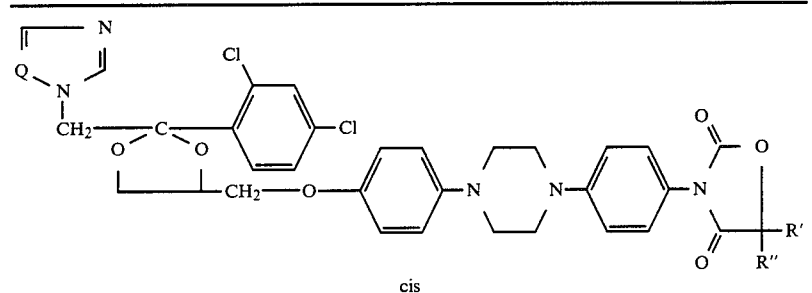

cis

| Compound No. | Q | R' | R" | mp. in °C. |
|---|---|---|---|---|
| 15 | N | CH₃ | H | 188.5 |
| 16 | N | CH₃ | CH₃ | 203.4 |
| 17 | CH | CH₃ | CH₃ | 214.1 |
| 18 | N | 2,4-Cl₂—C₆H₃ | H | 136.5 |
| 19 | CH | CH₃ | H | 173.6 |
| 20 | CH | 2,4-Cl₂—C₆H₃ | H | 142.0 |
| 21 | N | C₂H₅ | C₂H₅ | 157.8 |
| 22 | CH | C₂H₅ | CH₃ | 193.2 |
| 23 | N | C₂H₅ | CH₃ | 144.9 |
| and |  |  |  |  |
| 24 | CH | C₂H₅ | C₂H₅ | 140.4 |

EXAMPLE XLI

A mixture of 4.2 parts of 3-[4-[4-(4-hydroxyphenyl)-1-piperazinyl]phenyl]-1-(1-methylethyl)-2,4-imidazolidinedione, 4.3 parts of cis-2-(2,4-dichlorophenyl)-2-(1H-imidazol-1-ylmethyl)-1,3-dioxolane-4-methanol methanesulfonate (ester), 1.4 parts of potassium carbonate and 120 parts of 4-methyl-2-pentanone was stirred and refluxed for 72 hours. The reaction mixture was cooled and poured onto water. The product was extracted with dichloromethane. The extract was washed with water, dried, filtered and evaporated. The residue was purified by column chromatography over silica gel using a mixture of trichloromethane and methanol (99.5:0.5 by volume) as eluent. The pure fractions were collected and the eluent was evaporated. The residue was crystallized from 4-methyl-2-pentanone. The product was filtered off and dried at 120° C., yielding 1.9 parts (25%) of cis-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-1-(1-methylethyl)-2,4-imidazolidinedione; mp. 177.6° C. (compound 25).

EXAMPLE XLII

A mixture of 3.4 parts of 1-[4-[4-(4-hydroxyphenyl)-1-piperazinyl]phenyl]-3-methyl-2,4-imidazolidinedione, 5.6 parts of cis-2-(2,4-dichlorophenyl)-2-(1H-1,2,4-triazol-1-ylmethyl)-1,3-dioxolane-4-methanol methanesulfonate (ester), 2.8 parts of potassium carbonate, 20 parts of dimethyl sulfoxide and 64 parts of 1-butanol was stirred and refluxed for 3 hours. After cooling, 200 parts of water were added. The precipitated product was filtered off, washed with water and with 1-butanol, dried and purified by column-chromatography over silica gel using a mixture of trichloromethane and methanol (99.5:0.5 by volume) as eluent. The pure fractions were collected and the eluent was evaporated. The residue was crystallized from 160 parts of 1-butanol, yielding 2.1 parts (33%) of cis-1-[4-[4-[4-[[2-(2,4-dichlorophenyl)-2-(1H-1,2,4-triazol-1-ylmethyl)-1,3-dioxolane-4-yl]methoxy]phenyl]-3-methyl-2,4-imidazolidinedione; mp. 236.8° C. (compound 26).

In a similar manner there were also prepared:
cis-1-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-3-methyl-2,4-imidazolidinedione; mp. 237.9° C. (compound 27).

EXAMPLE XLIII

A mixture of 3.6 parts of 1-[4-[4-(4-hydroxyphenyl)-1-piperazinyl]phenyl]-3-(1-methylethyl)-2,4-imidazolidinedione, 5.5 parts of cis-2-(2,4-dichlorophenyl)-2-(1H-1,2,4-triazol-1-ylmethyl)-1,3-dioxolane-4-methanol methanesulfonate (ester), 2 parts of potassium carbonate and 160 parts of 1-butanol was stirred and refluxed for 3 hours. Then there was added another portion of 2.5 parts of cis-2-(2,4-dichlorophenyl)-2-(1H-1,2,4-triazol-1-ylmethyl)-1,3-dioxolane-4-methanol methanesulfonate (ester) and stirring at reflux was continued for 2 hours. The reaction mixture was cooled and 200 parts of water were added. Upon stirring, the precipitated product was filtered off and crystallized from 1-butanol, yielding 4.2 parts (65%) of cis-1-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-3-(1-methylethyl)-2,4-imidazolidinedione; mp. 227.1° C. (compound 28).

Following the same procedure and using equivalent amounts of the appropriate starting materials there were also prepared:

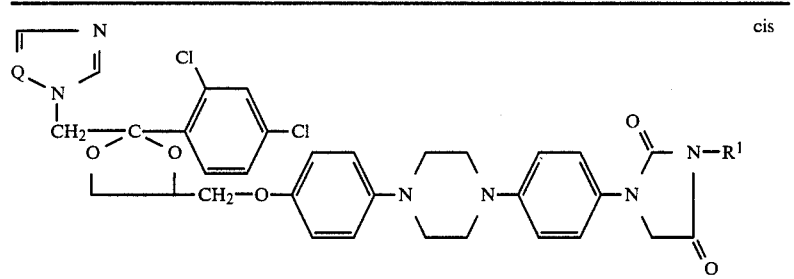

| Compound No. | Q | R¹ | mp. in °C. |
| --- | --- | --- | --- |
| 29 | CH | (CH$_3$)$_2$CH | 232.2 |
| 30 | N | n.C$_4$H$_9$ | 180.7 |
| 31 | CH | C$_2$H$_5$ | 235.4 |
| 32 | N | C$_2$H$_5$ | 228.6 |
| 33 | N | n.C$_3$H$_7$ | 195.4 and |
| 34 | CH | n.C$_3$H$_7$ | 199.5 |

EXAMPLE XLIV

A mixture of 5 parts of 1-[4-[4-(4-hydroxyphenyl)-1-piperazinyl]phenyl]-3-methyl-2-imidazolidinone, 8,7 parts of cis-2-(2,4-dichlorophenyl)-2-(1H-1,2,4-triazol-1-ylmethyl)-1,3-dioxolane-4-methanol methanesulfonate (ester), 3 parts of potassium carbonate and 160 parts of 1-butanol was stirred and refluxed overnight. The reaction mixture was cooled and 100 parts of water were added. The precipitated product was filtered off, dried and purified by column chromatography over silica gel using a mixture of trichloromethane and methanol (99:1 by volume) as eluent. The pure fractions were collected and the eluent was evaporated. The residue was crystallized from 1-butanol, yielding 7.8 parts (82%) of cis-1-[ 4-[4-[4-[[2-(2,4-dichlorophenyl)-2-(1H-1,2,4-triazol-1-ylmethyl)-1,3-dioxlan-4-yl]methoxy]phenyl]-1-piperazinyl]phenyl]-3-methyl-2-imidazolidinone; mp. 205.8° C. (compound 35).

Following the same procedure and using equivalent amounts of the appropriate starting materials there were also prepared:

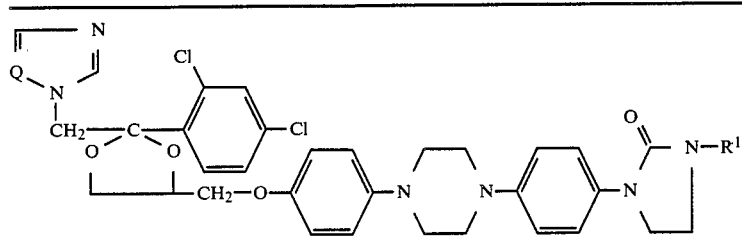

| Compound No. | Q | R¹ | mp. in °C. |
|---|---|---|---|
| 36 | N | $C_2H_5$ | 198.3 |
| 37 | CH | $C_2H_5$ | 205.3 |
| 38 | CH | $n.C_4H_9$ | 159.5 |
| 39 | N | $n.C_3H_7$ | 179.8–181.0 |
| 40 | CH | $n.C_3H_7$ | 189.2–191.3 |
| 41 | CH | $i.C_3H_7$ | 209.8–217.5 |
| 42 | N | $i.C_3H_7$ | 199.0–200.0 |
| 43 | CH | $CH_3$ | 215.4 |

In a similar manner there were also prepared:

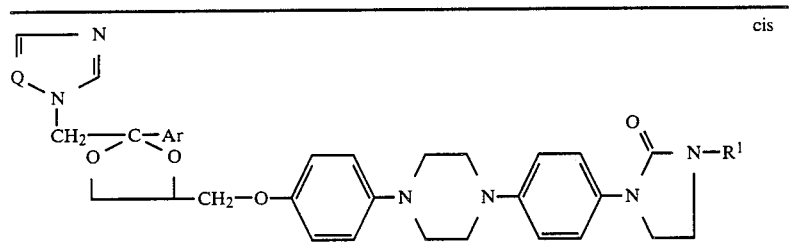

| Comp. No. | Q | Ar | R¹ | mp. in °C. |
|---|---|---|---|---|
| 44 | N | $2,4-Cl_2-C_6H_3$ | $n.C_4H_9$ | 152.2 |
| 45 | N | $4-Cl-C_6H_4$ | $n.C_3H_7$ | 194.3 |
| 46 | N | $2-Br, 4-Cl-C_6H_3$ | $n.C_3H_7$ | 181.0 |
| 47 | CH | $4-F-C_6H_4$ | $n.C_3H_7$ | 175.1 |
| 48 | N | $2-Cl-C_6H_4$ | $n.C_3H_7$ | 162.2 |
| 49 | N | $4-Br-C_6H_4$ | $n.C_3H_7$ | 201.5 and |
| 50 | CH | $2-Cl, 4-F-C_6H_3$ | $n.C_3H_7$ | 161.6 |

EXAMPLE XLV

A mixture of 3.3 parts of 4-[4-[4-[(3-butyltetrahydro-1,3-thiazin-2-ylidene)amino]phenyl]-1-piperazinyl]-phenol, 4.2 parts of cis-2-(2,4-dichlorophenyl)-2-(1H-1,2,4-triazol-1-ylmethyl)-1,3-dioxolane-4-methanol methanesulfonate(ester), 1.4 parts of potassium carbonate and 160 parts of 2-propanol was stirred and refluxed for 3 days. Another portion of 2.1 parts of cis-2-(2,4-dichlorophenyl)-2-(1H-1,2,4-triazol-1-ylmethyl)-1,3-dioxolane-4-methanol methanesulfonate (ester) was added and stirring was continued for 2 days at reflux temperature. After cooling, 300 parts of water were added. The precipitated product was filtered off, washed with water and 2-propanol, dried, filtered and evaporated. The residue was purified by filtration over silica gel using a mixture of trichloromethane and methanol (99:1 by volume) as eluent. The pure fractions were collected and the eluent was evaporated. The residue was crystallized from 4-methyl-2-pentanone. The product was filtered off and dried, yielding 3.8 parts (66%) of cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(3-butyltetrahydro-2H-1,3-thiazin-2-ylidene)benzenamine; mp. 190.8° C. (compound 51).

EXAMPLE XLVI

A mixture of 3 parts of 4-[4-[4-[(3-methyl-2(3H)-thiazolyliden)amino]phenyl]-1-piperazinyl]phenol, 3.5 parts of cis-2-(2,4-dichlorophenyl)-2-(1H-imidazol-1-ylmethyl)-1,3-dioxolane-4-methanol methanesulfonate(ester), 1.4 parts of potassium carbonate and 160 parts of 2-propanol was stirred and refluxed over weekend. Another portion of 3.5 parts of cis-2-(2,4-dichlorophenyl)-2-(1H-imidazol-1-ylmethyl)-1,3-dioxolane-4-methanol methanesulfonate(ester) and 1.4 parts of potassium carbonate was added and stirring was continued for 24 hours at reflux. After cooling, 200 parts of water were added. The precipitated product was filtered off, washed with water and 2-propanol and purified by column chromatography over silica gel using a mixture of trichloromethane and methanol (99:1 by volume) as eluent. The pure fractions were collected and the eluent was evaporated. The residue was crystallized from 1-butanol, yielding 4.1 parts (74%) of cis-4-[4-[4-[[2-(2,4-dichlorophenyl)-2-(1H-imidazol-1-ylmethyl)-1,3-dioxolan-4-yl]methoxy]phenyl]-1-piperazinyl]-N-(3-methyl-2(3H)thiazol ylidene)benzenamine; mp. 192.3° C. (compound 52).

In a similar manner there were also prepared:
cis-4-[4-[4-[[2-(2,4-dichlorophenyl)-2-(1H-1,2,4-triazol-1-ylmethyl)-1,3-dioxolan-4-yl]methoxy]phenyl]-1- piperazinyl]-N-(3-ethyl-2(3H)thiazolylidene)benzenamine; mp. 196.8° C. (compound 53);

cis-4-[4-[4-[[2-(2,4-dichlorophenyl)-2-(1H-imidazol-1-ylmethyl)-1,3-dioxolan-4-yl]methoxy]phenyl]-1-piperazinyl]-N-(3-ethyl-2(3H)-thiazolylidene)benzenamine; mp. 163.0° C. (compound 54);

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(3-methyl-2(3H)-thiazolylidene)benzenamine; mp. 177.5° C. (compound 55);

cis-4-[4-[4-[[2-(2,4-dichlorophenyl)-2-(1H-imidazol-1-ylmethyl)-1,3-dioxolan-4-yl]methoxy]phenyl]-1-piperazinyl]-N-(3-(1-methylpropyl)2(3H)-thiazolylidene)benzenamine; mp. 160.4° C. (compound 56);

cis-4-[4-[4 -[[2-(2,4-dichlorophenyl)-2-(1H-1,2,4-triazol-1-ylmethyl)-1,3-dioxolan -4-yl]methoxy]phenyl]-1-piperazinyl]-N-(3-(1-methylpropyl)-2(3H)thiazolylidene)benzenamine; mp. 151.4° C. (compound 57);

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-[3-(1-methylethyl)-2(3H)-thiazolylidene]benzenamine; mp. 176.1° C. (compound 58) ; and cis-4-[4-[4-[[2-(2,4-dichlorophenyl)-2-(1H-imidazol-1-ylmethyl)-1,3-dioxolan-4-yl]methoxy]phenyl]-1-piperazinyl-]-N-[3-(1-methylethyl)-2(3H)-thiazolylidene]benzenamine; mp. 178.6° C. (compound 59).

EXAMPLE XLVII

A mixture of 0.5 parts of bromoethane, 4 parts of cis-3-[4-[4-[4-[[2-(2,4-dichlorophenyl)-2-(1H-imidazol-1-ylmethyl)-1,3-dioxolan-4-ylmethoxy]phenyl]-1-piperazinyl]phenyl]-2,4-imidazolidinedione, 0.7 parts of potassium hydroxide and 100 parts of dimethyl sulfoxide was stirred for one hour at room temperature. The reaction mixture was poured onto water. The product was extracted with dichloromethane. The extract was washed with water, dried, filtered and evaporated. The residue was purified by column chromatography over silica gel using a mixture of trichloromethane and methanol (99.5–0.5 by volume) as eluent. The pure fractions were collected and the eluent was evaporated. The residue was crystallized from 4-methyl-2-pentanone, yielding 1.8 parts (43%) of cis-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-1-ethyl-2,4-imidazolidinedione; mp. 199.6° C. (compound 60).

EXAMPLE XLVIII

A mixture of 5 parts of cis-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-5-methyl-2,4-imidazolidinedione, 0.38 parts of a sodium hydride dispersion 50% and 100 parts of dimethyl sulfoxide was stirred till foaming had ceased. 1.01 Parts of 1-bromopropane were added and stirring was continued for 1 hour at room temperature. The reaction mixture was poured onto water. The product was extracted with dichloromethane. The extract was washed with water, dried, filtered and evaporated. The residue was purified twice by column chromatography over silica gel using first a mixture of trichloromethane and methanol (99:1 by volume) and then a mixture of trichloromethane and methanol (99.5:0.5 by volume) as eluent. The pure fractions were collected and the eluent was evaporated. The residue was crystallized from ethanol, yielding 2.4 parts (44%) of cis-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-5-methyl-1-propyl-2,4-imidazolidinedione mp. 133.7° C. (compound 61).

In a similar manner there were also prepared:

cis-1-butyl-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-5-methyl-2,4-imidazolidinedione; mp. 132.1° C. (compound 62);

cis-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-1-ethyl-5-methyl-2,4-imidazolidinedione; mp. 159.6° C. (compound 63).

cis-3-[4-[4-[4-[[2-(2,4-dichlorophenyl)-2-(1H-1,2,4-triazol-1-ylmethyl) -1,3-dioxolan-4-yl]methoxy]phenyl]-1-piperazinyl]phenyl]-1,5-dimethyl-2,4-imidazolidinedione; mp. 171.8° C. (compound 64)

cis-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-1-ethyl-5-methyl-2,4-imidazolidinedione; mp. 154.5° C. (compound 65).

cis-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-5-methyl-1-propyl-2,4-imidazolidinedione; mp. 142.0° C. (compound 66);

cis-1-butyl-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-5-methyl-2,4-imidazolidinedione; mp. 123.8° C. (compound 67); and cis-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-1,5-dimethyl-2,4-imidazolidinedione; mp. 194.3° C. (compound 68).

EXAMPLE IL

A mixture of 1 part of bromoethane, 3.5 parts of cis-3-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-5,5-dimethyl-2,4-imidazolidinedione, 0.5 parts of potassium hydroxide and 50 parts of dimethyl sulfoxide was stirred overnight at room temperature. The reaction mixture was poured onto water. The product was extracted with dichloromethane. The extract was washed with water, dried, filtered and evaporated. The residue was crystallized from methanol, yielding 3.2 parts (88%) of cis-3-[4-[4-[4-[[2 -(2,4-dichlorophenyl)-2-(1H-1,2,4-triazol-1-ylmethyl)-1,3-dioxolan-4-yl]methoxy]phenyl]-1-piperazinyl]phenyl]-1-ethyl-5,5-dimethyl-2,4-imidazolidinedione; mp. 165.0° C. (compound 70).

In a similar manner there were also prepared:

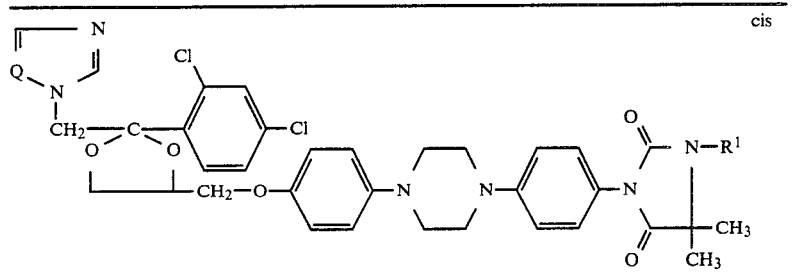

| Comp. No. | Q | R¹ | mp. in °C. |
|---|---|---|---|
| 70 | N | i.C3H7 | 129.6 |
| 71 | N | CH3 | 180.7 |
| 72 | N | n.C3H7 | 203.4 |
| 73 | N | n.C4H9 | 182.6 |
| 74 | CH | CH3 | 228.5 |
| 75 | CH | C2H5 | 190.6 |
| 76 | CH | n.C3H7 | 103.0 |
| 77 | CH | i.C3H7 | 125.6 |
| 78 | CH | n.C4H9 | 133.0 |
| 79 | CH | C2H5O(CH2)2 | 133.0 |
| 80 | CH | CH3O(CH2)2 | 152.6 |
| 81 | CH | n.C3H7O(CH2)2 | 145.6 |
| 82 | CH | i.C3H7O(CH2)2 | 149.7 |
| 83 | CH | i.C3H7—CH2 | 144.1 |
| 84 | CH | n.C5H11 | 79.2 |
| 85 | CH | CH3OCH2 | 122.1 |
| 86 | CH | C2H5(CH3)CH | 109.9 |
| 87 | CH | C3H7(CH3)CH | 129.1 |
| 88 | CH | i.C3H7(CH2)2 | 187.4 |
| 89 | CH | C3H5 | 111.1 |
| 90 | N | CH3O(CH2)2 | 179.5 |
| 91 | N | n.C3H7—(CH2)2 | 163.0 |
| 92 | CH | CH2=CH—CH2 | 119.7 |
| 93 | N | i.C3H7O(CH2)2 | 126.8 |
| 94 | CH | i.C2H5O(CH2)2 | 151.2 |
| 95 | CH | 2-Cl—4-pyrimidinyl | 190.6 |
| 96 | N | C2H5(CH3)CH | 150.1 |
| 97 | N | 2-Cl—4-pyrimidinyl | 196.5 |
| 98 | N | C3H5CH2 | 186.1 |
| 99 | N | i.C3H7CH2 | 193.2 |
| 100 | CH | CH3OCH2 | 122.1 |
| 101 | N | i.C3H7(CH2)2 | 176.9 |
| 102 | N | n.C5H11 | 163.0 and |
| 103 | CH | HC≡C—CH2 | 199.8 |

EXAMPLE L

A mixture of 1 part of ethyl hydrazinecarboxylate, 5 parts of cis-phenyl [4-[4-[4-[2-(2,4-dichlorophenyl)-2-(1H-1,2,4-triazol-1-ylmethyl)-1,3-dioxolan-4-ylmethoxy]phenyl]-1-piperazinyl]phenyl]carbamate, 1 part of N,N-dimethyl-4-pyridinamine and 100 parts of 1,4-dioxane was stirred and refluxed overnight. The reaction mixture was cooled and poured onto water. The product was extracted with dichloromethane. The extract was washed with water, dried, filtered and evaporated. The residue was crystallized from 4-methyl-2-pentanone. The product was filtered off and stirred in a mixture of 40 parts of 2-propanol and 75 parts of water with 7.5 parts of a sodium hydroxide solution 50% till all solid enters solution. The solution was neutralized with acetic acid and the product was extracted with dichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was triturated in 2-propanone. The product was filtered off and dried for 48 hours at 140° C., yielding 2.5 parts (53%) of cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-1,2,4-triazolidine-3,5-dione; mp. 210.8° C. (compound 104).

In a similar manner there was also prepared:
cis-4-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-1,2,4-triazolidine-3,5-dione; mp. 256.0° C. (compound 105).

EXAMPLE LI

A mixture of 1.46 parts of A, 4 parts of cis-4-[4-[4-[[2-(2,4-dichlorophenyl) -2-(1H-imidazol-1-ylmethyl)-1,3-dioxolan-4-yl]methoxy]phenyl]-1-piperazinyl]-phenyl]-1,2,4-triazolidine-3,5-dione, 1 part of potassium hydroxide and 100 parts of dimethyl sulfoxide was stirred for 2 hours at room temperature. The reaction mixture was poured onto water and the product was extracted with dichloromethane. The extract was washed with water, dried, filtered and evaporated. The residue was purified by column chromatography over silica gel using a mixture of trichloromethane and methanol (99.5:0.5 by volume) as eluent. The pure fractions were collected and the eluent was evaporated. The residue was crystallized from 4-methyl-2-pentanone, yielding 2.2 parts (51%) of cis-4-[4-[4-[[2-(2,4-dichlorophenyl)-2-(1H-imidazol-1-ylmethyl)-1,3-dioxolan-4-yl]methoxy]phenyl]-1-piperazinyl]phenyl]-1,2-diethyl-1,2,4-triazolidine-3,5-dione; mp. 180.4° C. (compound 106).

Following the same procedure and using equivalent amounts of the appropriate starting materials there were also prepared:

cis-4-[4-[4-[[2-(2,4-dichlorophenyl)-2-(1H-imidazol-1-ylmethyl)-1,3-dioxolan-4-yl]methoxy]phenyl]-1-piperazinyl]phenyl]-1,2-dipropyl-1,2,4-triazolidine-3,5-dione; mp. 150.7° C. (compound 107);

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-1,2-diethyl-1,2,4-triazolidine-3,5-dione; mp. 163.5° C. (compound 108);

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-1,2-dimethyl-1,2,4-triazolidine-3,5-dione; mp. 199.8° C. (compound 109);

cis-1,2-dibutyl-4-[4-[4-[[2-(2,4-dichlorophenyl)-2-(1H-imidazol-1-ylmethyl)-1,3-dioxolan-4-yl]methoxy]phenyl]-1-piperazinyl]phenyl]-1,2,4-triazolidine-3,5-dione; mp. 141.4° C. (compound 110);

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-1,2-dipropyl-1,2,4-triazolidine-3,5-dione; mp. 139.1° C. (compound 111);

cis-1,2-butyl-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]- 1,2,4-triazolidine-3,5-dione; mp. 120.1° C. (compound 112) ; and cis-4-[4-[4-[[2-(2,4-dichlorophenyl)-2-(1H-imidazol-1-ylmethyl)-1 3-dioxolan-4-yl]methoxy]phenyl]-1-piperazinyl]phenyl]-1,2-dimethyl-1,2,4 -triazolidine-3,5-dione; mp. 204.7° C. (compound 113) .

EXAMPLE LII

To a stirred mixture of 8.5 parts of cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]-phenyl]-1,2,4-triazolidine-3,5-dione, 1.2 parts of potassium hydroxide and 100 parts of dimethyl sulfoxide were added dropwise 2.5 parts of 1,3-dibromopropane. Upon completion, stirring was continued for 30 minutes. The reaction mixture was poured onto water. The product was extracted with dichloromethane. The extract was washed with water, dried, filtered and evaporated. The residue was purified by column chromatography over silica gel using a mixture of trichloromethane and methanol (98:2 by volume) as eluent. The pure fractions were collected and the eluent was evaporated. The residue was crystallized from 1-butanol, yielding 5.1 parts of cis-2-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]dihydro-1H ,5H-pyrazolo[1,2-a][1,2,4]triazole-1,3(2H)-dione; mp. 223.8° C. (compound 114).

In a similar manner there were also prepared:

cis-2-[4-[4-[4-[[2-(2,4-dichlorophenyl)-2-(1H-imidazol-1-ylmethyl)-1,3-dioxolan-4-yl]methoxy]-phenyl]-1-piperazinyl]phenyl]dihydro-1H,5H-pyrazolo[1,2-a][1,2,4]triazole-1,3(2H)-dione;mp. 249.2° C; (compound 115);

cis-2-[4-[4-[4-[[2-(2,4-dichlorophenyl)-2-(1H-1,2,4-triazol-1-ylmethyl)-1,3-dioxolan-4-yl]methoxy]-phenyl]-1-piperazinyl]phenyl]5,6,7,8-tetrahydro-1H-[1,2,4]triazolo[1,2-a]pyridazine-1,3(2H)-dione; mp. 194.7° C. (compound 116); and cis-2-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-5,6,7,8-tetrahydro-1H-[1,2,4]-triazolo[1,2-a]pyridazine-1,3(2H)-dione; mp. 200.5° C. (compound 117).

EXAMPLE LIII

To a stirred suspension of 5.4 parts of cis-N-[4-[4-[4--[[2-(2,4-dichlorophenyl)-2-(1H-1,2,4-triazol-1-ylmethyl)-1,3-dioxolan-4-yl]methoxy]phenyl]-1-piperazinyl]phenyl]-N'-(2-hydroxyethyl)-N'-methylthiourea in 260 parts of dichloromethane was added dropwise a solution of 1.92 parts of thionyl chloride in 130 parts of dichloromethane. The temperature was kept below 0° C. by cooling in an ice/saltbath. Upon completion, stirring was continued for 2 hours at room temperature. The reaction mixture was neutralized with a sodium hydrogen carbonate solution. The layers were separated. The organic layer as purified by filtration over silica gel using a mixture of trichloromethane and methanol (99:1 by volume) as eluent. The pure fractions were collected and the eluent was evaporated. The residue was crystallized from ethanol, yielding 4.7 parts (89%) of cis-4-[4-[4-[[2-(2,4-dichlorophenyl)-2-(1H-1,2,4-triazol-1-ylmethyl)-1,3-dioxolan-4-yl]methoxy]-phenyl]-1-piperazinyl]-N-(3-methyl-2-thiazolidinylidene)benzenamine; mp. 164.5° C. (compound 118).

Following the same procedure and using equivalent amounts of the appropriate starting materials there were also prepared:

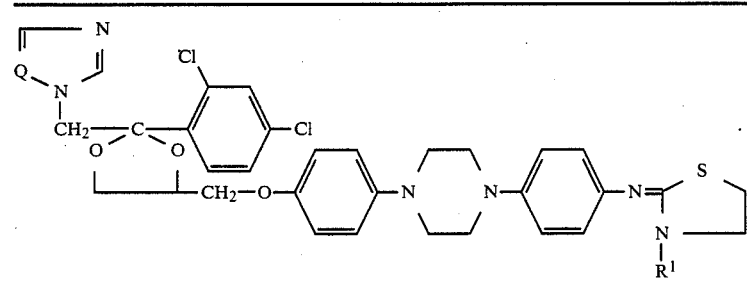

| Compound No. | Q | R¹ | Salt or base form | mp. in °C. |
|---|---|---|---|---|
| 119 | CH | $C_2H_5$ | base | 142.7 |
| 120 | CH | $i.C_3H_7$ | base | 183.1 |

-continued

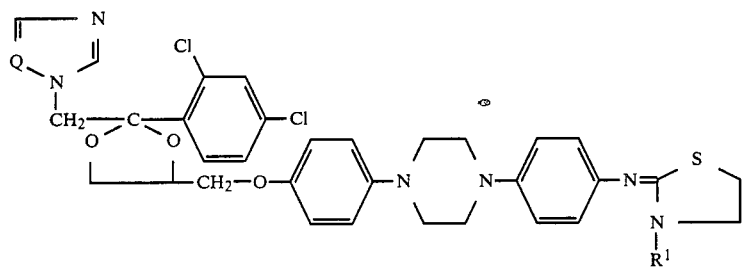
cis

| Compound No. | Q | R¹ | Salt or base form | mp. in °C. |
|---|---|---|---|---|
| 121 | N | C₂H₅ | C₂H₅OH | 148.1 |
| 122 | N | C₂H₅(CH₃)CH | base | 125.5 |
| 123 | CH | i.C₅H₁₁ | base | 104.9–108.4 |
| 124 | CH | n.C₄H₉ | base | 64.9–73.6 |
| 125 | N | n.C₃H₇ | base | 173.3–175.6 |
| 126 | N | i.C₃H₇ | base | 179.1–180.1 |
| 127 | CH | CH₃ | base | 152.8 |
| 128 | N | i.C₄H₉ | base | 189.7 |
| 129 | CH | n.C₃H₇ | base | 149.2 |
| 130 | N | n.C₅H₁₁ | base | 167.7 |
| 131 | CH | n.C₅H₁₁ | base | 117.7 |
| 132 | CH | (C₂H₅)₂CH | base | 86.3 |
| 133 | CH | C₂H₅(CH₃)CHCH₂ | base | 126.4 |
| 134 | N | (C₂H₅)₂CH | base | 123.2 |
| 135 | N | n.C₄H₉ | base | 176.6 |
| 136 | N | C₂H₅(CH₃)CHCH₂ | base | 172.1 |
| 137 | N | i.C₅H₁₁ | base | 183.5 |
| 138 | N | n.C₃H₇(CH₃)CH | base | 166.1 |
| 139 | N | C₆H₅ | base | 165.2 and |
| 140 | CH | .C₆H₅ | H₂O | 97.7 |

EXAMPLE LIV

To a stirred and cooled (ice-bath) solution of 5 parts of cis-N-[4-[4-[4-[[2-(2,4-dichlorophenyl)-2-(1H-1,2,4-triazol-1-ylmethyl)1,3-dioxolan-4-yl]methoxy]phenyl]-1-piperazinyl]phenyl]-N'-(1-ethylpropyl)-N'-(2-hydroxyethyl)urea in 130 parts of dichloromethane were added 2.4 parts of thionyl chloride and the whole was stirred for 1 hour at room temperature. The reaction mixture was neutralized with a sodium hydrogen carbonate solution and the layers were separated. The organic phase was filtered over silica gel using a mixture of trichloromethane and methanol (99.5:0.5 by volume) as eluent. The filtrate was evaporated and the residue was crystallized from ethanol, yielding 4.3 parts (89%) of cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-[3-(1-ethylpropyl)-2-oxazolidinylidene]benzenamine; mp. 178.1° C. (compound 141).

Following the same procedure and using equivalent amounts of the appropriate starting materials there were also prepared:

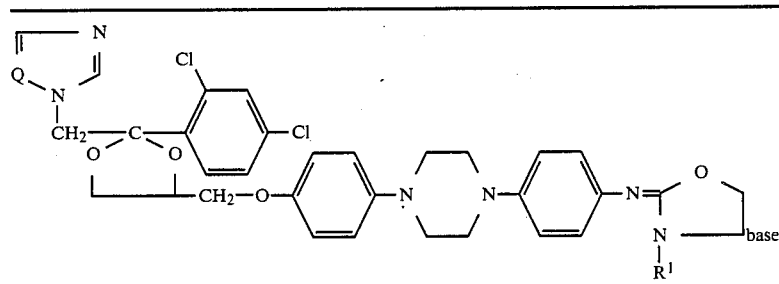
cis

| Compound No. | Q | R¹ | mp. in °C. |
|---|---|---|---|
| 142 | CH | C₂H₅ | 192.5 |
| 143 | N | CH₃ | 187.0 |
| 144 | N | C₂H₅ | 149.1 |
| 145 | N | n.C₃H₇ | 144.0 |
| 146 | N | n.C₄H₉ | 135.6 |
| 147 | N | i.C₃H₇ | 189.1 |
| 148 | N | C₂H₅(CH₃)CH | 175.8 |
| 149 | N | i.C₅H₁₁ | 149.7 |
| 150 | N | C₂H₅(CH₃)CHCH₂ | 119.1 |
| 151 | N | i.C₄H₉ | 149.8 |
| 152 | N | n.C₃H₇(CH₃)CH | 150.1 and |

-continued

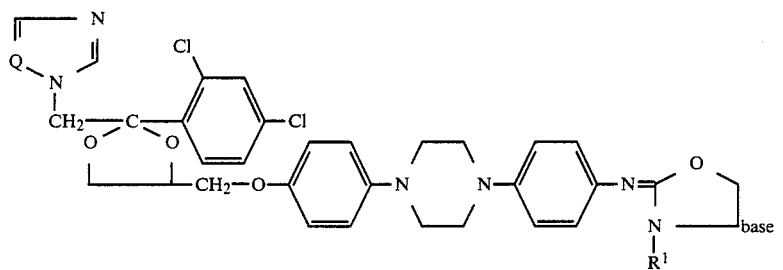

| Compound No. | Q  | R¹          | mp. in °C. |
|--------------|----|-------------|------------|
| 153          | CH | C₂H₅(CH₃)CH | 143.3      |

EXAMPLE LV

To a stirred and cooled (ice/salt bath) mixture of 8 parts of thionyl chloride and 195 parts of dichloromethane were added portionwise 8.8 parts of cis-N-[4-[-4-[4-[[2-(2,4-dichlorophenyl)-2-(1H-imidazol-1-ylmethyl)-1,3-dioxolan-4-yl]methoxy]phenyl]-1-piperazinyl]phenyl]-N'-(2-hydroxyethyl)-N'-(1-methylpropyl)thiourea at a temperature below 0° C. Upon completion, stirring was continued for 1 hour. The reaction mixture was neutralized with a sodium hydrogen carbonate solution and the layers were separated. The organic phase was filtered over silica gel using a mixture of trichloromethane and methanol (99:1 by volume) as eluent. The filtrate was evaporated and the residue was purified by column-chromatography (HPLC) over silica gel using a mixture of methylbenzene and ethanol (90:10 by volume) as eluent. The pure fractions were collected and the eluent was evaporated. The residue was separated by HPLC over silica gel using a mixture of trichloromethane and methanol (97:3 by volume) as eluent.

The first fraction was collected and the eluent was evaporated. The residue was crystallized from a mixture of 4-methyl-2-pentanone and 2,2'-oxybispropane, yielding 0.8 parts (10%) of cis-1-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-3-(1-methylpropyl)-2-imidazolidinethione; mp. 161.8° C. (compound 154).

The second fraction was collected and the eluent was evaporated. The residue was crystallized from a mixture of 4-methyl-2-pentanone and 2,2'-oxybispropane, yielding 0.8 parts (10%) of cis-N-[3-(1-methylpropyl)-2-thiazolidinylidene]-4-[4-[4-[[2-(2,4-dichlorophenyl)-2-(1H-imidazol-1-ylmethyl)-1,3-dioxolan-4-yl]methoxy]phenyl]-1-piperazinyl]benzenamine; mp. 121.0° C. (compound 155).

In a similar manner there were also prepared:
cis-1-[4-[4-[4-[[2-(2,4-dichlorophenyl)-2-(1H-imidazol-1-ylmethyl)-1,3-dioxolan-4-yl]methoxy]phenyl]-1-piperazinyl]-phenyl]-3-(2-methylpropyl)-2-imidazolidinethione; mp. 165.3° C. (compound 156); and cis-4-[4-[4-[[2-(2,4-dichlorophenyl)-2-(1H-imidazol-1-ylmethyl)-1,3-dioxolan-4-yl]methoxy]phenyl]-1-piperazinyl]-N-[3-(2-methylpropyl)-2-thiazolidinylidene]benzenamine; mp. 134.6° C. (compound 157).

EXAMPLE LVI

To a stirred solution of 3.2 parts of thionyl chloride in 130 parts of dichloromethane was added dropwise a solution of 5.5 parts of cis-N'-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]phenyl]-N-ethyl-N-(3-hy droxypropyl)urea in 260 parts of C while cooling in an ice/salt bath at a temperature below 0° C. Upon completion, stirring was continued for 1 hour and the whole was allowed to reach room temperature. The mixture was neutralized with a sodium hydrogen carbonate solution and the layers were separated. The organic layer was purified twice by column chromatography over silica gel using first a mixture of trichloromethane and methanol (98:2 by volume) and a mixture of trichloromethane and methanol (95:5 by volume) and then a mixture of trichloromethane and methanol (95:5 by volume) as eluent. The pure fractions were collected and the eluent was evaporated. The residue was crystallized from ethanol, yielding 2.6 parts (45%) of cis-4-[4-[-4-[[2-(2,4-dichlorophenyl)-2-(1H-1,2,4-triazol-1-yl-methyl)-1,3-dioxolan-4-yl]methoxy]phenyl]-1-piperazinyl]-N-(3-ethyl-tetrahydro-2H-1,3-oxazin-2-ylidene)benzenamine ethanol(1:1); mp. 101.5° C. (compound 158).

EXAMPLE LVII

To a stirred solution of 2.4 parts of thionyl chloride in 130 parts of dichloromethane was added dropwise a solution of 7.3 parts of cis-N'-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N-ethyl-N-(3-hyd roxypropyl)thiourea in 260 parts of dichloromethane while cooling in an ice/salt bath at a temperature below 0° C. Upon completion, stirring was continued for 1 hour. The mixture was neutralized with a sodium hydrogen carbonate solution and the layers were separated. The organic layer was evaporated. The residue was purified by column chromatography over silica gel using a mixture of trichloromethane and methanol (99:1 by volume) as eluent. The second fraction was collected and the eluent was evaporated. The residue was crystallized from ethyl acetate. The product was filtered off and dried in a dry-pistol at 90° C., yielding 3.1 parts (43%) of cis-4-[4-[4-[[2-(2,4-dichlorophenyl)-2-(1H-1,2,4-triazol-1-yl-methyl)-1,3-dioxolan-4-yl]methoxy]phenyl]-1-piperazinyl]-N-(3-ethyl-tetrahydro-2H-1,3-thiazin-2-ylidene)benzenamine; mp. 160.4° C. (compound 159).

In a similar manner there were also prepared:

cis-4-[4-[4-[[2-(2,4-dichlorophenyl)-2-(1H-imidazol-1-ylmethyl)-1,3-dioxolan-4-yl]methoxy]phenyl]-1-piperazinyl]-N-(3-ethyl-tetrahydro-2H-1,3-thiazin-2-ylidene)benzenamine; mp. 131.5° C. (compound 160); and cis-4-[4-[4-[[2-(2,4-dichlorophenyl)-2-(1H-imidazol-1-ylmethyl)-1,3-dioxolan-4-yl]methoxy]phenyl]-1-piperazinyl]-N-(3,4,5,6-tetrahydro-3-(1-methylethyl)-2H-1,3-thiazin-2-ylidene)benzenamine; mp. 180.3° C. (compound 161).

EXAMPLE LVIII

To a stirred solution of 3.2 parts of thionyl chloride in 130 parts of dichloromethane was added dropwise a solution of 8 parts of cis-N-butyl-N'-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]phenyl]-N-(3-hydroxypropyl)thiourea in 260 parts of C at a temperature below 10° C. Upon completion, stirring was continued for one hour. The reaction mixture was neutralized with a sodium hydrogen carbonate solution. The layers were separated. The organic phase was evaporated. The residue was purified twice by column chromatography over silica gel using first a mixture of trichloromethane and methanol (99:1 by volume) and then a mixture of trichloromethane and methanol (98:2 by volume) as eluent. The pure fractions were collected and the eluent was evaporated. The residue was crystallized from ethanol. The product was filtered off and dried, yielding 2.7 parts (34%) of cis-1-butyl-3-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]phenyl]-3,4,5,6-tetrahydro-2(1H)-pyrimidinethione; mp. 159.1° C. (compound 162).

In a similar manner there were also prepared:

cis-1-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-3-ethyltetrahydro-2(1H)-pyrimidinethione; mp. 168.8° C. (compound 163);

cis-1-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-3-ethyltetrahydro-2(1H)-pyrimidinethione; mp. 194.2° C. (compound 164); and cis-1-butyl-3-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-tetrahydro-2(1H)-pyrimidinethione; mp. 163.7° C. (compound 165).

EXAMPLE LIX

A solution of 7 parts of cis-N'-[4-[4-[4-[[2-(2,4-dichlorophenyl)-2-(1H-imidazol-1-ylmethyl)-1,3-dioxolan-4-yl]methoxy]phenyl]-1-piperazinyl]phenyl]-N-(2,2-dimethoxyethyl)-N-ethylthiourea in 60 parts of formic acid was stirred for 1 hour. The whole was evaporated. The residue was dissolved in dichloromethane. The reaction mixture was neutralized with a sodium hydrogen carbonate solution. The layers were separated. The organic layer was dried, filtered and evaporated. The residue was crystallized from 4-methyl-2-pentanone and 2,2'-oxybispropane, yielding 6 parts (89%) of cis-4-[-4-[4-[[2-(2,4-dichlorophenyl)-2-(1H-imidazol-1-ylmethyl)-1,3-dioxolan-4-yl]methoxy]phenyl]-1-piperazinyl]-N-(3-ethyl-5-methoxy-2-thiazolidinylidene)benzenamine; mp. 155.0° C. (compound 166).

In a similar manner there were also prepared:

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-[5-methoxy-3-(phenylmethyl)-2-thiazolidinylidene]benzenamine; mp. 86.8° C. (compound 167);

cis-4-[4-[4-[[2-(2,4-dichlorophenyl)-2-(1H-imidazol-1-ylmethyl)-1,3-dioxolan-4-yl]methoxy]phenyl]-1-piperazinyl]-N-(5-methoxy-3-methyl-2-thiazolidinylidene)benzenamine; mp. 156.6° C. (compound 168);

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(5-methoxy-3-methyl2-thiazolidinylidene)benzenamine; mp. 127.6° C. (compound 169);

cis-4-[4-[4-[[2-(2,4-dichlorophenyl)-2-(1H-imidazol-1-ylmethyl)-1,3-dioxolan-4-yl]methoxy]phenyl]1-piperazinyl]-N-[5-methoxy-3-(1-methylprop yl)-2-thiazolidinylidene]benzenamine 1-butanol(1:1); mp. 88.1° C. (compound 170);

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(5-methoxy-3-ethyl-2-thiazolidinylidene)benzenamine; mp. 134.5° C. (compound 171);

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-[5-methoxy-3-(1-methylpropyl)-2-thiazolidinylidene]benzenamine; mp. 131.3° C. (compound 172);

cis-4-[4-[4-[[2-(2,4-dichlorophenyl)-2-(1H-1,2,4-triazol-1-yl-methyl)-1,3-dioxolan-4-yl]methoxy]phenyl]-1-piperazinyl]-N-[5-methoxy-3-(1-methylethyl)-2-thiazolidinylidene]benzenamine; mp. 164.0° C. (compound 173); and cis-4-[4-[4-[[2-(2,4-dichlorophenyl)-2-(1H-imidazol-1-ylmethyl)-1,3-dioxolan-4-yl]methoxy]phenyl]-1-piperazinyl]-N-[5-methoxy-3-(1-methyleth yl)-2-thiazolidinylidene]benzenamine; mp. 137.0° C. (compound 174).

EXAMPLE LX

A mixture of 4.1 parts of 1-butyl-3-[4-[4-(4-hydroxyphenyl)-1-piperazinyl]phenyl]-2,4-imidazolidinedione, 6.5 parts of cis-2-(4-bromophenyl)-2-(1H-1,2,4-triazol-1-ylmethyl)-1,3-dioxolane-4-methanol methanesulfonate(ester) ethanedioate (1:1), 6.0 parts of potassium carbonate, 160 parts of 1-propanol and 25 parts of 1,4-dioxane was stirred and refluxed for 3 days. The reaction mixture was diluted with water and the product was extracted three times with dichloromethane. The combined organic layers were washed with water, dried and evaporated in vacuo. The residue was purified by column chromatography over silica gel using a mixture of trichloromethane and methanol (99:1 by volume) as eluent. The pure fractions were collected and the eluent was evaporated. The residue was crystallzed from 4-methyl-2-pentanone. The product was filtered off and dried, yielding 1.7 parts (25%) of propyl cis-[4-[4-[4-[[2-(4-bromophenyl)-2-(1H-1,2,4-triazol-1-ylmethyl)-1,3-dioxolan-4-yl]methoxy]phenyl]-1-piperazinyl]phenyl]-carbamate; mp. 214.4° C. (compound 175).

In a similar manner there were also prepared:

cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(1-methyl-2-imidazolidinylidene)benzenamine; mp. 161.9° C. (compound 176); and cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(1-ethyl-2-imidazolidinylidene)benzenamine; mp. 184.0° C. (compound 177).

EXAMPLE LXI

A mixture of 5 parts of cis-N'-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-N-ethyl-N-[2-(ethylamino)ethyl]thiourea, 2.2 parts of mercury(II) oxide and 160 parts of acetonitrile was stirred and refluxed for 20 hours. Another portion of 0.8 parts of B were added and stirring at reflux was continued for 24 hours. The reaction mixture was filtered hot over Hyflo and the filtrate was evaporated. The residue was dried, filtered and evaporated. The residue was purified by column chromatography over silica gel using a mixture of trichloromethane and methanol (99:1 by volume) as eluent. The pure fractions were collected and the eluent was evaporated. The residue was crystallized from acetonitrile (activated charcoal), yielding 2.9 parts (61%) of cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(1,3-diethyl-2-imidazolidinylidene)benzenamine; mp. 91.7° C. (compound 178).

In a similar manner there were also prepared:
cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]-N-(3-phenyl-2-oxazolidin ylidene)benzenamine; mp. 133.2° C. (compound 179); and cis-4-[4-[4-[[2-(2,4-dichlorophenyl)-2-(1H-imidazol-1-ylmethyl)-1,3-dioxolan-4-yl]methoxy]phenyl]-1-piperizinyl]-N-(1,3-diethyl-2-imidazolidinylidene)benzenamine ; mp. 178.0° C. (compound 180).

EXAMPLE LXII

To a stirred solution of 5.1 parts of ethanedioyl dichloride in 300 parts of trichloromethane was added dropwise a warm solution of 6.4 parts of cis-N-butyl-N'-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]pheny l]urea in 150 parts of trichloromethane. Upon completion, the whole was heated to reflux and stirring was continued for 1 hour at reflux temperature. Another 2.9 parts of ethanedioyl dichloride was added and stirring at reflux was continued for 2 hours. After cooling, 30 parts of potassium carbonate were added and water was added dropwise carefully (foaming). The organic layer was separated. The aqueous phase was extracted with trichloromethane. The combined organic layers were washed with water, dried, filtered and evaporated. The residue was purified by filtration over silica gel using a mixture of methylbenzene and ethanol (97:3 by volume) as eluent. The pure fractions were collected and the eluent was evaporated. The residue was crystallized from 1-butanol. The product was filtered off and dried in vacuo at 60° C., yielding 5.8 parts (83%) of cis-1-butyl-3-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]-phenyl]-b 2,4,5-imidazolidinetrione; mp. 150.4° C. (compound 181).

Following the same procedure and using equivalent amounts of the appropriate starting materials there were also prepared:

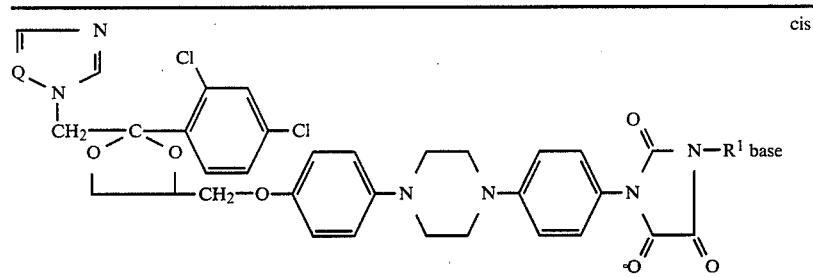

| Compound No. | Q | R¹ | mp. in °C. |
|---|---|---|---|
| 182 | CH | CH$_3$ | 209.3 |
| 183 | N | CH$_3$ | 208.8 |
| 184 | N | C$_2$H$_5$ | 171.8 |
| 185 | N | n.C$_3$H$_7$ | 152.4 |
| 186 | N | i.C$_3$H$_7$ | 191.6 |
| 187 | CH | i.C$_4$H$_9$ | 212.3 |
| 188 | N | i.C$_4$H$_9$ | 172.7 |
| 189 | N | n.C$_5$H$_{11}$ | 150.2 |
| 190 | CH | n.C$_3$H$_7$ | 198.7 |
| 191 | N | i.C$_5$H$_{11}$ | 164.6 |
| 192 | CH | i.C$_5$H$_{11}$ | 145.3 |
| 193 | CH | t.C$_4$H$_9$ | 206.8 |
| 194 | N | C$_2$H$_5$(CH$_3$)CH | 159.7 |
| 195 | CH | n.C$_5$H$_{11}$ | 169.7 |
| 196 | CH | C$_3$H$_7$(CH$_3$)CH | 137.0 |
| and |  |  |  |
| 197 | CH | (C$_2$H$_5$)$_2$CH | 157.4 |

EXAMPLE LXIII

To a stirred mixture of 6.5 parts of cis-N-[4-[4-[4-[2-(2,4-dichlorophenyl)-2-(1H-imidazol-1-ylmethyl)-1,3-dioxolan-4-ylmethoxy]-phenyl]-1-piperazinyl]phenyl ]-N'-ethylurea, 0.5 parts of N,N-dimethyl-4-pyridinamine, 50 parts of pyridine and 65 parts of dichloromethane were added dropwise 1.57 parts of ethanedioyl dichloride at room temperature. Upon completion, stirring was continued overnight at reflux temperature. Another portion of 0.75 parts of ethanedioyl dichloride was added and the whole was stirred and refluxed. The reaction mixture was poured onto 600 parts of water. The organic layer was separated. The aqueous phase was extracted with dichloromethane. The organic layer was washed with water, dried, filtered and evaporated. The residue was stirred in 2-propanone. The precipitate was filtered off and the filtrate was evaporated. The residue was purified by column chromatography over silica gel using a mixture of trichloromethane and methanol (99:1 by volume) as eluent. The first fraction was collected and the eluent was evaporated. The residue was stirred in 4-methyl-2-pentanone. The product was filtered off and dried in vacuo at 60° C., yielding 1.4 parts (19%) of cis-1-[4-[4-[4-[[2-(2,4-dichlorophenyl)-2-(1H-imidazol-1-ylmethyl)-1,3-dioxolan-4-yl]methox y]-phenyl]-1-piperazinyl]phenyl]-3-ethyl-2,4,5-imidazolidinetrione; mp. 212.5° C. (compound 198).

In a similar manner there were also prepared:
cis-1-[4-[4-[4-[[2-(2,4-dichlorophenyl)-2-(1H-imidazol-1-yl-methyl)-1,3-dioxolan-4-yl]methoxy]phenyl]-1-piperazinyl]-phenyl]-3-(1-methylet hyl)-2,4,5-imidazolidinetrione; mp. 218.2° C. (compound 199);
cis-1-butyl-3-[4-[4-[4-[[2-(2,4-dichlorophenyl)-2-(1H-imidazol-1-yl-methyl)-1,3-dioxolan-4-yl]methoxy]-phenyl]-1-piperazinyl]phenyl]-2,4,5- imidazolidinetrione; mp. 173.5° C. (compound 200).

EXAMPLE LXIV

To a stirred mixture of 60 parts of formic acid and 50 parts of water were added 10 parts of cis-N-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]p henyl]-1-methylhydrazinecarbothioamide. The whole was stirred overnight at room temperature. This solution was added dropwise to 240 parts of concentrate hydrochloric acid. Upon completion, stirring was continued for 1 hour. The whole was neutralized with sodium hydrogen carbonate. The product was extracted with dichloromethane. The extract was dried, filtered and evaporated. The residue was purified by column chromatography over silica gel using a mixture of trichloromethane and methanol (99.5:0.5 by volume) as eluent. The pure fractions were collected and the eluent was evaporated. The residue was crystallized from 4-methyl-2-pentanone, yielding 4.4 parts (43%) of cis-4-[4-[4-[[2-(2,4-dichlorophenyl)-2-(1H-1,2,4-triazol-1-yl-methyl)-1,3-dioxolan-4-yl]methoxy]-phenyl]-1-piperazinyl]-N-(3-methyl-1,3,4-thiadiazol-2(3H)-ylidene)benzenamine; mp. 175.2° C. (compound 201).

What we claim is:
1. A chemical compound having the formula

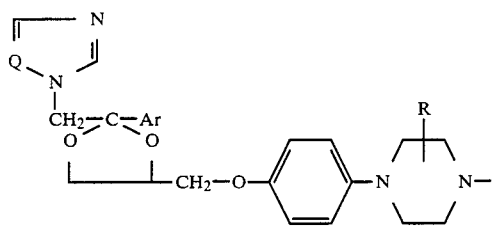

(XII-a-1)

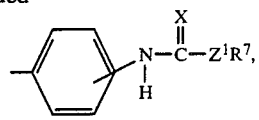

a pharmaceutically acceptable acid-addition salt or a stereochemically isomeric forms thereof, wherein
Q is N or CH;
Ar is phenyl or substituted phenyl, said substituted phenyl having from 1 to 3 substituents each independently selected from the group consisting of halo, lower alkyl, lower alkyloxy, nitro, amino and trifluoromethyl, provided that trinitrophenyl is excluded;
R is hydrogen or lower alkyl; and
X is O, S or $NR^2$ said $R^2$ being hydrogen or lower alkyl;
$Z^1$ is O or $NR^8$, said $R^8$ being hydrogen, Ar or lower alkyl optionally substituted by Ar, and
$R^7$ is hydrogen, Ar, amino or lower alkyl optionally substituted by a member selected from the group consisting of hydroxy, Ar-amino, lower alkylamino or carboxy or substituted with up to two lower alkyloxy radicals, provided that:
$Z^1$ is other than O where $R^7$ is hydrogen; and where $R^7$ is amino, $Z^1$ is other than NH or O.

2. A composition for combatting microorganisms comprising an inert carrier material and as an active ingredient an antimicrobially effective amount of a compound having the formula

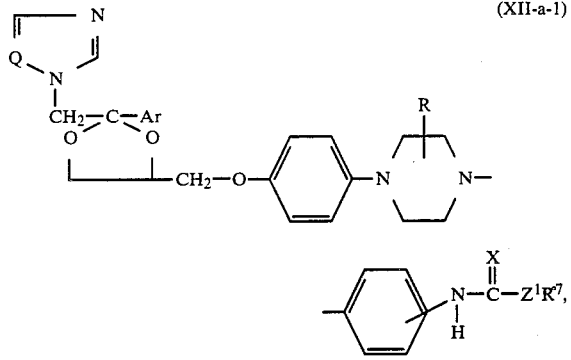

(XII-a-1)

a pharmaceutically acceptable acid-addition salt or a stereochemically isomeric forms thereof, wherein
Q is N or CH;
Ar is phenyl or substituted phenyl, said substituted phenyl having from 1 to 3 substituents each independently selected from the group consisting of halo, lower alkyl, lower alkyloxy, nitro, amino and trifluoromethyl, provided that trinitrophenyl is excluded;
R is hydrogen or lower alkyl; and
X is O, S or $NR^2$, said $R^2$ being hydrogen or lower alkyl;
$Z^1$ is O or $NR^8$, said $R^8$ being hydrogen, Ar or lower alkyl optionally substituted by Ar, and
$R^7$ is hydrogen, Ar, amino or lower alkyl optionally substituted by a member selected from the group consisting of hydroxy, Ar-amino, lower alkylamino or carboxy or substituted with up to two lower alkyloxy radicals, provided that:
$Z^1$ is other than O where $R^7$ is hydrogen; and where $R^7$ is amino, $Z^1$ is other than NH or O.

3. A method of inhibiting and/or eliminating the development of fungi and bacteria in warm-blooded animals suffering from diseases caused by these fungi and/or bacteria by the systemic or topical administration of an antimicrobially effective amount of a compound having the formula

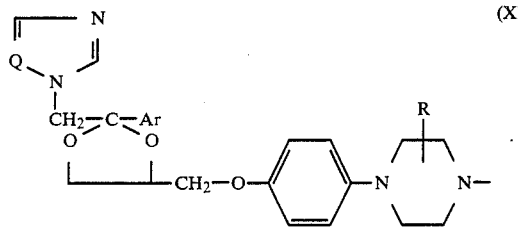

(XII-a-1)

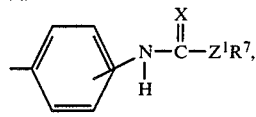

a pharmaceutically acceptable acid-addition salt or a stereochemically isomeric forms thereof, wherein Q is N or CH;

Ar is phenyl or substituted phenyl, said substituted phenyl having from 1 to 3 substituents each independently selected from the group consisting of halo, lower alkyl, lower alkyloxy, nitro, amino and trifluoromethyl, provided that trinitrophenyl is excluded;

R is hydrogen or lower alkyl; and

X is O, S or $NR^2$ said $R^2$ being hydrogen or lower alkyl;

$Z^1$ is O or $NR^8$, said $R^8$ being hydrogen, Ar or lower alkyl optionally substituted by Ar, and $R^7$ is hydrogen, Ar, amino or lower alkyl optionally substituted by a member selected from the group consisting of hydroxy, Ar-amino, lower alkylamino or carboxy or substituted with up to two lower alkyloxy radicals, provided that:

$Z^1$ is other than O where $R^7$ is hydrogen; and where $R^7$ is amino, $Z^1$ is other than NH or O.

* * * * *